US012121362B1

United States Patent
Pulkkinen et al.

(10) Patent No.: US 12,121,362 B1
(45) Date of Patent: Oct. 22, 2024

(54) NON-INTRUSIVE SLEEP EFFICIENCY ANALYSIS AND RECOMMENDATIONS USING HEART DATA

(71) Applicant: Amazon Technologies, Inc., Seattle, WA (US)

(72) Inventors: Pekka Pietari Pulkkinen, Sammamish, WA (US); Andreas Caduff, Clyde Hill, WA (US); Haithem Albadawi, Redmond, WA (US)

(73) Assignee: Amazon Technologies, Inc., Seattle, WA (US)

( * ) Notice: Subject to any disclaimer, the term of this patent is extended or adjusted under 35 U.S.C. 154(b) by 224 days.

(21) Appl. No.: 17/018,796

(22) Filed: Sep. 11, 2020

(51) Int. Cl.
*A61B 5/00* (2006.01)
*A61B 5/024* (2006.01)
*G16H 50/30* (2018.01)

(52) U.S. Cl.
CPC ........ *A61B 5/4815* (2013.01); *A61B 5/02416* (2013.01); *A61B 5/681* (2013.01); *A61B 5/7264* (2013.01); *G16H 50/30* (2018.01); *A61B 2562/0219* (2013.01)

(58) Field of Classification Search
CPC .......... A61B 2562/0219; A61B 5/4815; A61B 5/02416; A61B 5/681; A61B 5/7264; G16H 50/30
See application file for complete search history.

(56) References Cited

U.S. PATENT DOCUMENTS

| | | | |
|---|---|---|---|
| 2010/0069761 A1* | 3/2010 | Karst ...................... | A61B 5/029 600/484 |
| 2016/0027324 A1* | 1/2016 | Wisbey .................. | G16H 40/63 434/247 |
| 2016/0287122 A1* | 10/2016 | Heneghan .............. | A61B 5/113 |
| 2017/0347948 A1* | 12/2017 | Thein .................. | A61B 5/02416 |
| 2019/0000375 A1* | 1/2019 | Ferreira Dos Santos Da Fonseca ................... | A61B 5/11 |
| 2020/0061325 A1* | 2/2020 | Grashow ................ | A61B 5/374 |
| 2021/0369209 A1* | 12/2021 | Braun ................ | A61B 5/02416 |

* cited by examiner

*Primary Examiner* — Alyssa M Alter
*Assistant Examiner* — Jessandra F Hough
(74) *Attorney, Agent, or Firm* — Eversheds Sutherland (US) LLP

(57) ABSTRACT

Devices, systems, and methods are provided for non-intrusive sleep efficiency analysis and recommendations using heart data. A method may include receiving, by a device, photoplethysmography (PPG) data associated with a heart signal. The method may include determining a first portion of the PPG data that fails to exceed a threshold frequency and a second portion of the PPG data that exceeds the threshold frequency. The method may include determining a ratio of the first portion to the second portion. The method may include determining, based on the PPG data, an inspiratory flow, and determining, based on the ratio and the inspiratory flow, a forecasted sleep efficiency score. The method may include determining a recommended activity associated with increasing the forecasted sleep efficiency score. The method may include presenting the forecasted sleep efficiency score and the recommended activity.

20 Claims, 12 Drawing Sheets

NON-INTRUSIVE SLEEP EFFICIENCY ANALYSIS AND RECOMMENDATIONS USING HEART DATA

BACKGROUND

People increasingly are monitoring their activities and consumption habits to improve their health. Some activities that people may monitor include exercise, rest, and sedentary periods. People may be interested in how much time they are sleeping and the quality of their sleep. However, some methods of measuring a person's sleep are invasive and/or require a variety of equipment. Also, many methods of measuring a person's sleep are retrospective and do not predict a person's future sleep. Accordingly, there is a need for enhanced sleep efficiency analysis.

Figure 1:
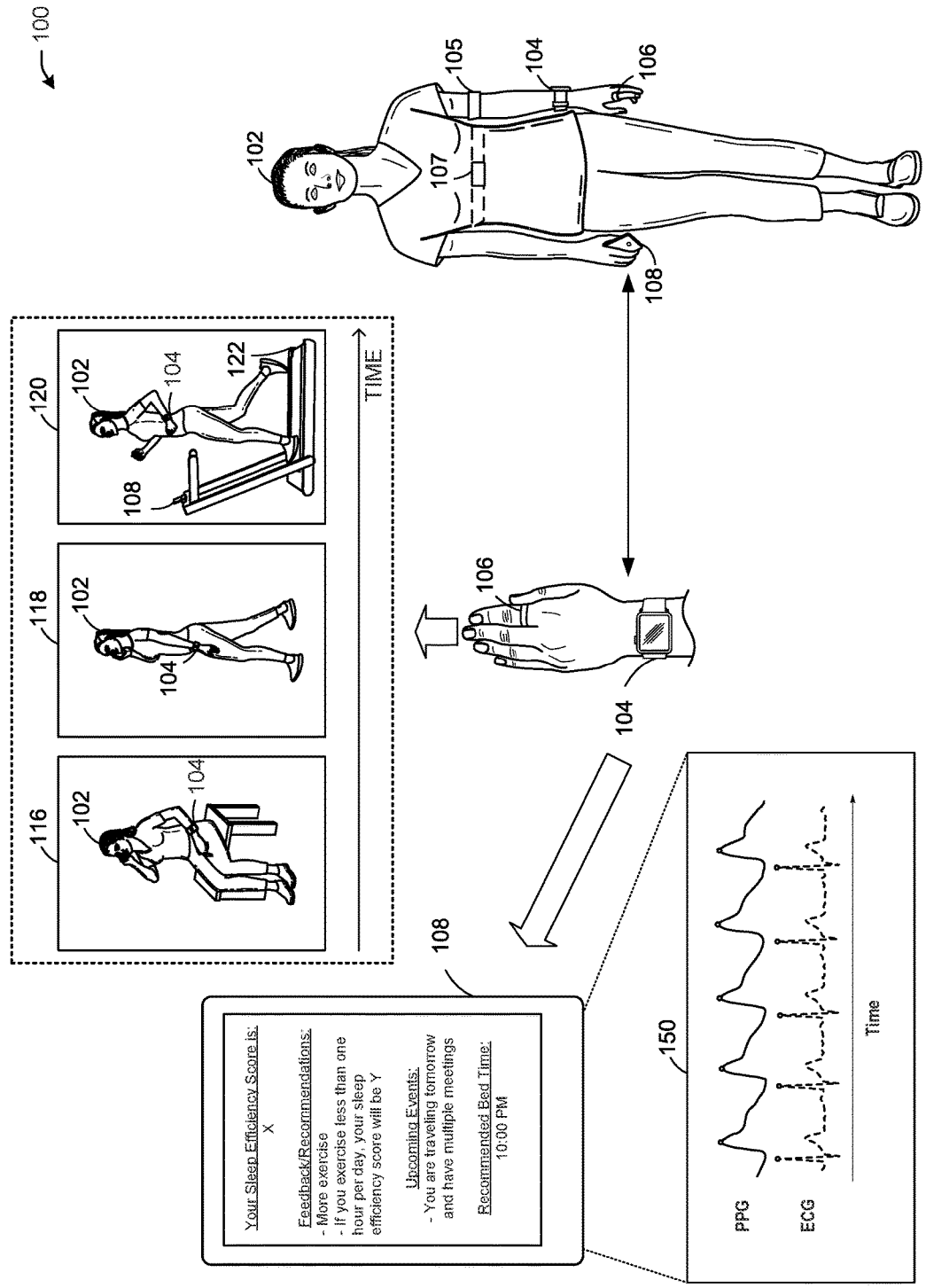
FIG. 1 illustrates an example system for sleep efficiency evaluations and recommendations, in accordance with one or more example embodiments of the present disclosure.

Certain implementations will now be described more fully below with reference to the accompanying drawings, in which various implementations and/or aspects are shown. However, various aspects may be implemented in many different forms and should not be construed as limited to the implementations set forth herein; rather, these implementations are provided so that this disclosure will be thorough and complete, and will fully convey the scope of the disclosure to those skilled in the art. Like numbers in the figures refer to like elements throughout. Hence, if a feature is used across several drawings, the number used to identify the feature in the drawing where the feature first appeared will be used in later drawings.

DETAILED DESCRIPTION

Overview

Example embodiments described herein provide certain systems, methods, and devices for non-intrusive sleep efficiency analysis and recommendations using heart data.

A person's activities may be evaluated in a variety of ways. For example, user device data, such accelerometer or other motion and/or location data, may provide an indication of a person's activity levels (e.g., whether the person with the user device moved a certain amount during a time period). Biometric data, such as heart rate (HR), breathing rate, pulse oximetry, body fat, hydration level, body temperature, blood sugar, and the like, may indicate whether a person is sleeping, sedentary, or active. The combination of device and biometric data may provide indications of activity levels of a person over a period of time.

Sleep efficiency is an important factor for a person's sleep quality. A comprehensive photoplethysmography (PPG) study may be required to measure heart data to determine a person's sleep efficiency (e.g., over eight hours), but such comprehensive studies may be intrusive, time-consuming, and expensive, often requiring a variety of equipment, and often requiring measurements to be performed while a person sleeps. Some sleep efficiency analyses may require a person in a sleep laboratory to wear electroencephalography (EEG) sensors and other sensors to identify epochs. The measurements may require the use of multiple probes placed on different locations of a person's body, and thoracic volume change may require a person to breath into a machine. Alternatively, using ECG data, beat-to-beat intervals may be measured, and based on the heart interval data, heart rate variability (HRV) metrics may be determined (e.g., a low-frequency to high-frequency ratio). HRV metrics may refer to variability between successive heart beats, such as during a R-R interval. Using the thoracic volume data, a peak inspiratory flow (PIF) may be determined. A person's sleep efficiency may be determined based on the PIF and the low-frequency to high-frequency ratio. However, even some less comprehensive PPG studies may be intrusive and may require expensive equipment. In addition, some techniques that evaluate a person while sleeping may not provide an indication of how a person may sleep in the future and may not take into account the effects that current or recent actions of the person (e.g., a person's activities) may have on the person's future sleep efficiency.

People therefore would benefit from enhanced non-intrusive sleep efficiency analysis and recommendations.

In one or more embodiments, a system may use PPG data detected by a device (e.g., a wearable device), and may determine HRV or breathing metrics based on the PPG data without requiring invasive equipment or methods. Using the HRV and breathing metrics, the system may estimate a person's sleep efficiency. Based on the person's sleep efficiency, the system may recommend activities, bed times, wake times, meals, and the like.

In one or more embodiments, the system may combine heart data with breathing data and device data (e.g., accelerometer data or other device data indicative of motion) to determine a person's anticipated sleep efficiency and to recommend activities, bed times, wake times, meals, and the like. However, the system may not need a user to breath into any particular equipment, but rather may determine breathing data from heart data (e.g., PPG data, pulse, etc.). Based on heart data and device motion data indicative of a person's activities, the system may predict a person's sleep score for an upcoming night (or other time). When the projected sleep score may be lower than a threshold score, the system may recommend that a person perform or not perform certain activities. For example, when the person has not exercised, the system may recommend that the person perform some exercise activity before going to bed in order to improve a sleep score. Activity data (e.g., indicating when a person exercised or was sedentary) may be indicated by motion data of a device and/or other inputs, such as biometric data, user inputs indicating activities performed by the user, and the like. When the person has been very active and/or has a busy or early schedule the next day (e.g., based on device calendar data, travel schedules, etc.), the system may recommend (e.g., based on previous positive influences on sleep efficiency for a user or other users) an early bed time to allow a person to have more rest. In this manner, the system may recommend actions and/or behavioral changes throughout the day so that a person may see what their sleep score is likely to be by performing or not performing certain actions. A person's activities may be identified based on device motion data, biometric data, user inputs, calendar data, and the like. The system may analyze other data such as stress and energy levels (e.g., as indicated by activities, tone of voice, biometric data, and the like). The system may determine a sleep score based on the other data in combination with PPG data.

In one or more embodiments, the system may analyze biometric data during a time period when a person is awake, but relatively still (e.g., when device motion data is below a threshold, and possibly above zero or another threshold to account for whether a person is still and awake or is asleep). In this manner, the system may analyze a person's activities and/or consumption while the person is awake, may forecast a sleep efficiency score for the upcoming evening, and may present information that may allow the person to adjust activities and/or consumption in a manner that is likely to improve sleep efficiency. The system may analyze biometric data during the time period that the person is awake, but relatively still. After forecasting a sleep efficiency score, the system may adjust future forecasts based on the accuracy of a forecasted sleep efficiency score (e.g., compared to the actual sleep efficiency determined after a person sleeps). Based on past activities and/or consumption and their effects on previous scores, the system may project sleep efficiency scores and identify behaviors that may positively and/or negatively impact sleep efficiency. The system may determine, based on metrics such as HRV metrics and/or inspiratory flow, a person's previous sleep score and/or a forecasted sleep score.

In one or more embodiments, heart data may be determined based on camera screening (e.g., during a video call). For example, there is an increasing use of smartphone camera-based vital sign monitoring. When a person is still in front of a device camera for a period of time (e.g., a few minutes), for example during a video call, a system may determine HRV metrics based on observations from the video call. For example, a system may include HF components that also may determine sleep efficiency similar to how sleep efficiency may be determined using PPG.

The above descriptions are for purposes of illustration and are not meant to be limiting. Numerous other examples, configurations, processes, etc., may exist, some of which are described in greater detail below. Example embodiments will now be described with reference to the accompanying figures.

Illustrative Processes and Use Cases

FIG. 1 illustrates an example system 100 for sleep efficiency evaluations and recommendations, in accordance with one or more example embodiments of the present disclosure.

Referring to FIG. 1, the system 100 may include a user 102 with multiple devices (e.g., device 104, device 105, device 106, device 107, device 108). For example, the user 102 may be wearing the device 104 (e.g., a wrist watch), the device 106 (e.g., a ring device), the device 105 (e.g., a wearable band), and/or the device 107 (e.g., a wearable band capable of detecting ECG data), and may be holding or carrying the device 108 (e.g., a smartphone). At step 116 (e.g., a time), the user 102 may be sedentary (e.g., sitting). At step 118 (e.g., a time), the user 102 may be walking (e.g., exercising lightly or moderately). At step 120, the user 102 may be jogging or running on a treadmill 122 (e.g., exercising moderately or vigorously). Step 116, step 118, and step 120 may represent different times throughout a day or multiple days (e.g., a week, month, etc.). The user 102 may be wearing or holding any one or more of the device 104, the device 105, the device 106, the device 107, and/or the device 108 at any of step 116, step 118, and step 120, or any one or more of the device 104, the device 106, and/or the device 108 may be otherwise monitoring, with user consent and consistent with appropriate laws, activity of the user 102 as explained further herein.

Still referring to FIG. 1, data received by any one or more of the device 104, the device 106, and/or the device 108 may include device motion data (e.g., accelerometer or other data indicative of motion). Any one or more of the device 104, the device 106, and/or the device 108 may analyze the device motion data to determine amounts of activities (e.g., walking, running, eating, sleeping, etc.) performed by the user 102 over a period of time (e.g., a week, a month, etc.). Any one or more of the device 104, the device 106, and/or the device 108 may determine the amounts of time that the user 102 exercised and/or spent sedentary. Any one or more of the device 104, the device 106, and/or the device 108 may determine the total and average number of steps (e.g., a daily or weekly total or average) that the user 102 performed over a time period. Any one or more of the device 104, the device 106, and/or the device 108 may receive heart data 150 (e.g., PPG data and/or ECG data as discussed further with respect to FIG. 2A), and may use the heart data 150 in combination with the device motion data and/or respiratory data (e.g., determined based on a correlation with the heart data 150 as explained further herein) to determine a past and/or projected sleep score, and/or to determine recommended activities, sleep times, wake times, and the like to present to the user 102 using any one or more of the device 104, the device 106, and/or the device 108. For example, as shown, any one or more of the device 104, the device 106, and/or the device 108 may present a sleep efficiency score, feedback and recommendations regarding exercise, consumption, and the like, recommended bed times and/or wake times, events that the person 102 has scheduled, and the like. In this manner, the heart data 150 may be detected non-invasively and used to project a sleep efficiency score and to determine recommendations to improve sleep efficiency. For example, the ECG data of the heart data may be detected by the device 107 or another of the devices shown.

In one or more embodiments, the ECG and PPG data of the heart data 150 may be detected by a single device/location, or may be detected by multiple devices and provided to a device for analysis and display. The heart data 150 may be determined without the need to touch the device with a hand or finger, for example, by relying on breathing data and/or HRV metrics as explained herein.

In one or more embodiments, the device 104, the device 105, the device 106, the device 107, and/or the device 108 may include a personal computer (PC), a smart home device, a wearable wireless device (e.g., bracelet, watch, glasses, ring, strap/band, etc.), a desktop computer, a mobile computer, a laptop computer, an Ultrabook™ computer, a notebook computer, a tablet computer, a server computer, a handheld computer, a handheld device, an internet of things (IoT) device, a sensor device, a PDA device, a handheld PDA device, an on-board device, an off-board device, a hybrid device (e.g., combining cellular phone functionalities with PDA device functionalities), a consumer device, a vehicular device, a non-vehicular device, a mobile or portable device, a non-mobile or non-portable device, a mobile phone, a cellular telephone, a PCS device, a PDA device which incorporates a wireless communication device, a mobile or portable GPS device, a DVB device, a relatively small computing device, a non-desktop computer, a "carry small live large" (CSLL) device, an ultra mobile device (UMD), an ultra mobile PC (UMPC), a mobile internet device (MID), an "origami" device or computing device, a device that supports dynamically composable computing (DCC), a context-aware device, a video device, an audio device, a media player, a smartphone, or the like.

Figure 2A:
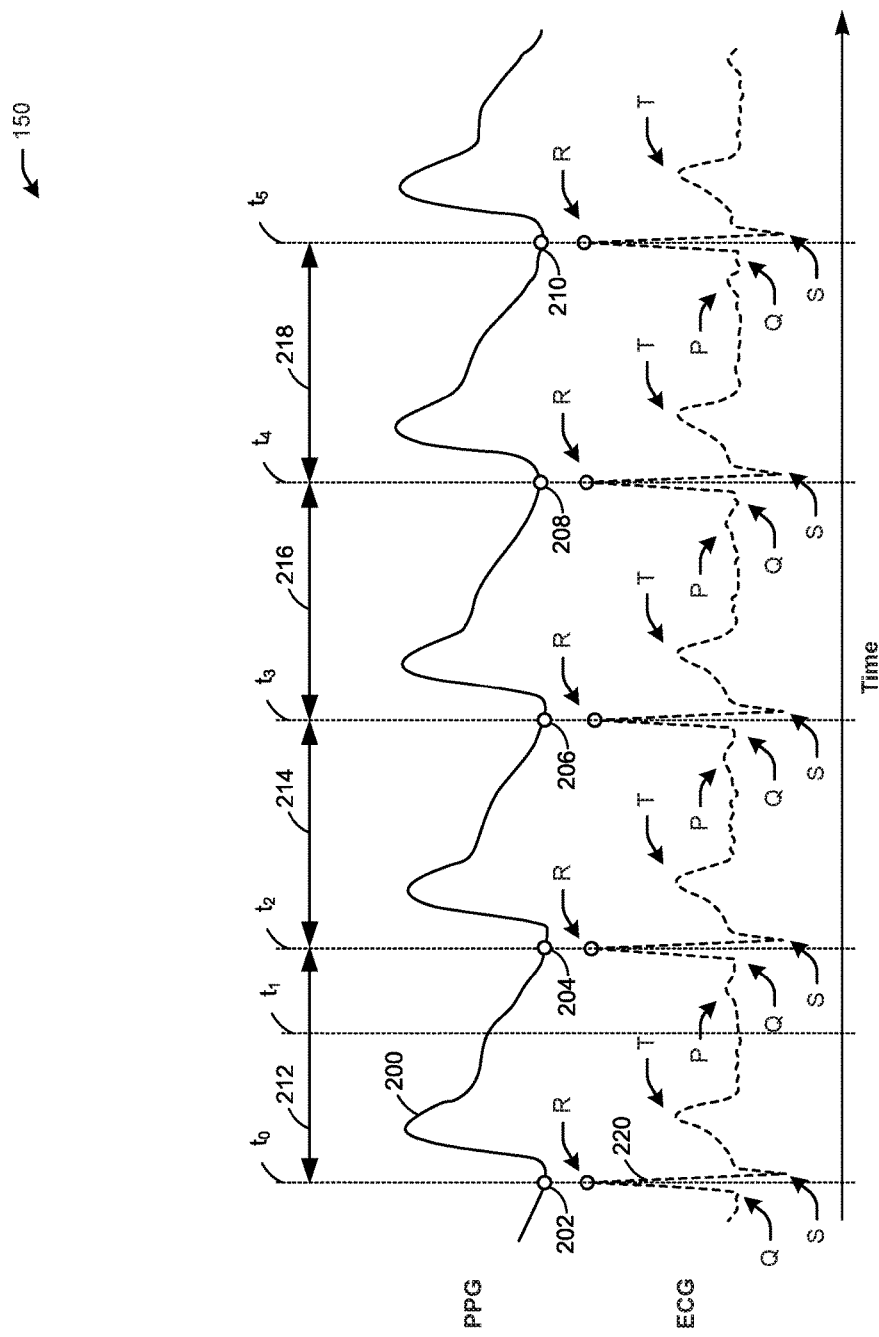
FIG. 2A illustrates example heart data for use in sleep efficiency evaluations and recommendations, in accordance with one or more example embodiments of the present disclosure.

FIG. 2A illustrates example heart data (e.g., the heart data 150 of FIG. 1) for use in sleep efficiency evaluations and recommendations, in accordance with one or more example embodiments of the present disclosure.

Referring to FIG. 2A, PPG data 200 is represented over time. The PPG data 200 may be detected by any of the device 104, the device 105, the device 106, the device 107, and/or the device 108 of FIG. 1 (e.g., wearable devices, bands, straps, finger devices, etc.). The PPG data 200 may be periodic. For example, data point 202, data point 204, data point 206, data point 208, and data point 210 may represent the same repeating data points for the PPG data 200. In particular, data period 212 may represent the time between the data point 202 and the data point 204 (e.g., a time period from time $t_0$ to time $t_2$). Data period 214 may represent the time between the data point 204 and the data point 206 (e.g., a time period from time $t_2$ to time $t_3$). Data period 216 may represent the time between the data point 206 and the data point 208 (e.g., a time period from time $t_3$ to time $t_4$). Data period 218 may represent the time between the data point 208 and the data point 210 (e.g., a time period from time $t_4$ to time $t_5$). The data periods may be the same or different in length as explained further with respect to FIG. 2B, and may represent the periodic nature of the PPG data 200.

Still referring to FIG. 2A, ECG data 220 is shown over time. While the device 104, the device 106, and/or the device 108 may not detect the ECG data 220, the PPG data 200 may correlate to the ECG data 220. For example, the ECG data 220 shows a PQRST heart wave, and the RR intervals (e.g., the time between respective R waves of the ECG data 220) may correspond to the data points 202-210 of the PPG data 200. In this manner, a periodic time period of the PPG data 200 may correspond to RR intervals of the ECG data 220. A full PQRST wave of the ECG data 220 is shown beginning shortly after time $t_1$.

In one or more embodiments, the device 104, the device 105, the device 106, the device 107, and/or the device 108 may determine two corresponding data points (e.g., of the same amplitude) from the PPG data 200, representing a repeating (e.g., periodic) time period. Based on the time period, the device 104, the device 106, and/or the device 108 may determine HRV metrics (e.g., as explained further with respect to FIG. 2C) and respiratory metrics (e.g., as explained further with respect to FIG. 2B). Using the metrics, the device 104, the device 105, the device 106, the device 107, and/or the device 108 may determine a person's sleep efficiency score. Using activity data (e.g., device motion data), the device 104, the device 106, and/or the device 108 may recommend activities, consumption, bed times, wake times, and the like.

Figure 2B:
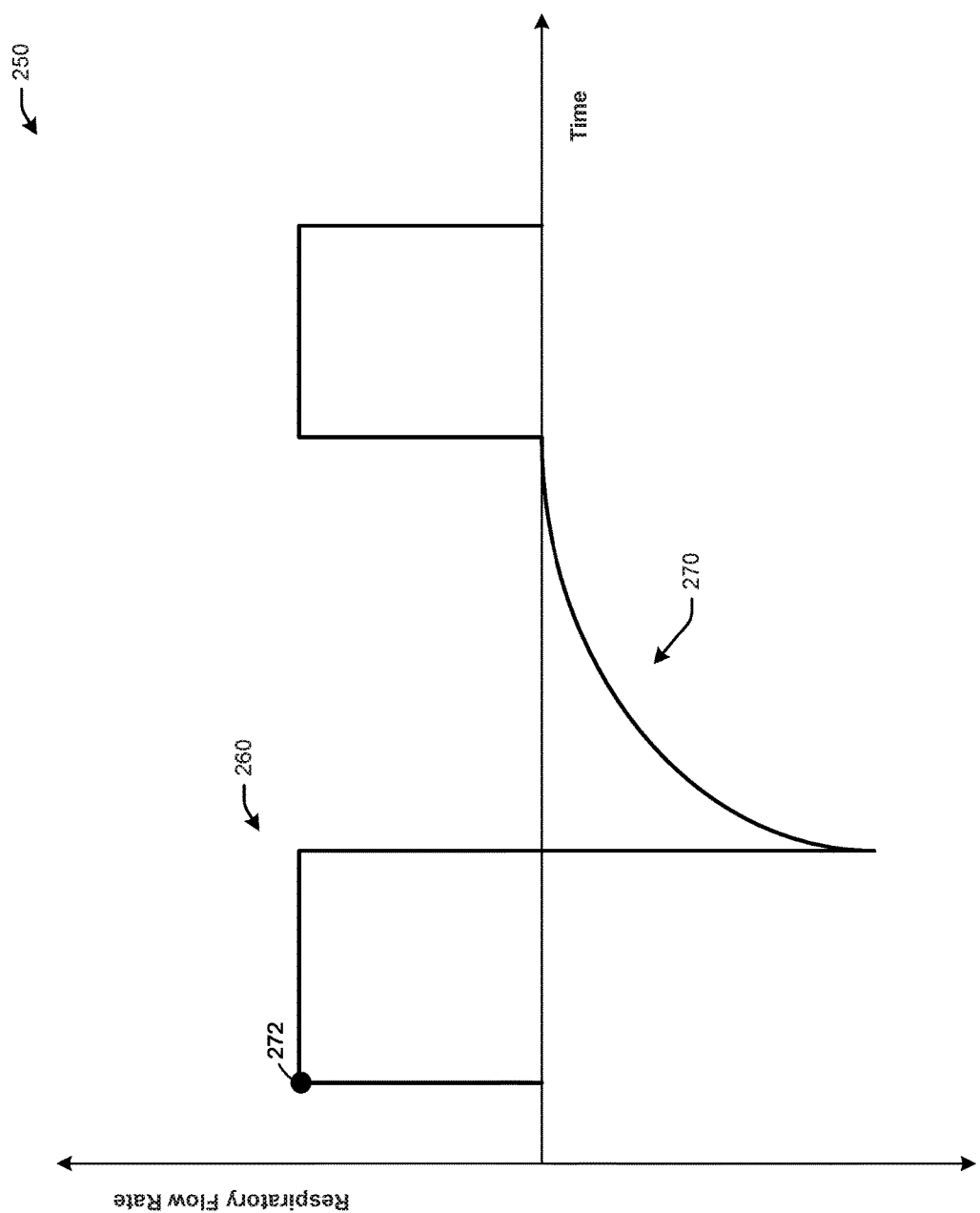
FIG. 2B illustrates example respiratory data for use in sleep efficiency evaluations and recommendations, in accordance with one or more example embodiments of the present disclosure.

FIG. 2B illustrates example respiratory data 250 for use in sleep efficiency evaluations and recommendations, in accordance with one or more example embodiments of the present disclosure.

Referring to FIG. 2B, the respiratory data 250 may represent an inhalation and expiration of the user 102 of FIG. 1. Based on the PPG data 200 of FIG. 2A, any of the device 104, the device 106, and/or the device 108 of FIG. 1 may use the intervals of the PPG data 200 to determine when the user 102 is inhaling or exhaling. Heart rate generally increases during inhalation and decreases during exhalation. Relatedly, the R-R interval is shorter during inspiration and longer during expiration. In this manner, longer R-R waves (or corresponding periods of a PPG signal) may be indicative of expiration, and shorter R-R waves may be indicative of inhalation, allowing for an identification of a person's respiration rate by identifying how often the person is inhaling and exhaling during a period of time. As such, the PIF 272 may be based on the R-R interval.

Still referring to FIG. 2B, the respiratory data 250 indicates a period 260 when the user 102 is inhaling, and a period 270 when the user 102 is exhaling. The maximum flow rate during the inhalation period 260 may refer to PIF 272. As explained further herein, the PIF 272 and other biometric data may be used to determine a sleep efficiency score for the user 102.

Figure 2C:
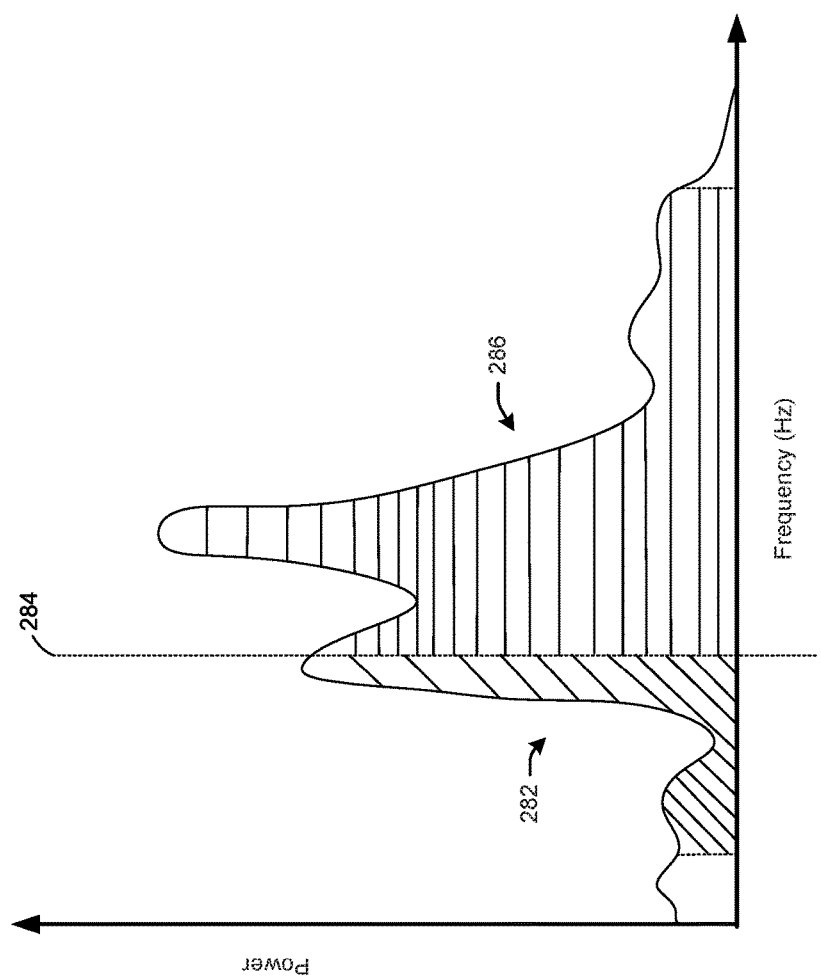
FIG. 2C illustrates example heart variability data for use in sleep efficiency evaluations and recommendations, in accordance with one or more example embodiments of the present disclosure.

FIG. 2C illustrates example heart variability data 280 for use in sleep efficiency evaluations and recommendations, in accordance with one or more example embodiments of the present disclosure.

Referring to FIG. 2C, the heart variability data 280 may be used to determine HRV metrics, such as low-frequency to high-frequency ratio (LF/HF ratio), referring to a ratio of the portion of the heart variability data 280 that is within a low frequency range to a portion of the heart variability data 280 that is in a high frequency range. A LF portion 282 may represent the heart variability data 280 that is below a threshold 284, and a HF portion 286 may represent the heart variability data 280 that is above the threshold 284. The LF/HF ratio may represent the ratio of the LF portion 282 to the HF portion 286, and may be determined by any of the device 104, the device 106, and/or the device 108 of FIG. 1. As explained further herein, the LF/HF ratio and other biometric data may be used to determine a sleep efficiency score for the user 102 of FIG. 1.

In one or more embodiments, the threshold 284 may be set at 0.15 Hz. The LF portion 282 may refer to the portion of the heart variability data 280 between 0.04 Hz and 0.15

Hz, and the HF portion 286 may refer to the portion of the heart variability data 280 between 0.15 Hz and 0.4 Hz.

In one or more embodiments, the LF/HF ratio may be based on the number of heart beats detected per interval. For example, the frequency ranges for HF and LF may be influenced by a breathing rate (e.g., beats per minute—bpm). Generally, when a person is relaxed, the person's breathing is slower and deeper than when the person is stressed or is exerting significant energy (e.g., exercising). During inspiration, R-R intervals may be shortened, and heart rate may increase. During exhalation, R-R intervals may be longer. Heart rate and time between heart beats therefore may vary, and HRV metrics may indicate the variations. For example, physical and emotional stress may cause an increased heart rate, resulting in less time between heart beats. In this manner, slower breathing with higher HRV may indicate low stress, and faster breathing with lower HRV may indicate higher stress. As discussed further herein, the correlation between stress and HRV may be used to determine sleep efficiency.

Sleep efficiency is a commonly and widely used measure to objectively evaluate sleep quality. Monitoring sleep efficiency may provide significant information about health conditions. To assess autonomic activity, heart rate variability and breathing parameters may be analyzed. Using extracted parameters as explanatory variables (e.g., the PIF 272, the LF/HF ratio, etc.), stepwise multiple linear regression analyses and k-fold cross-validation tests may be performed by any of the device 104, the device 106, and/or the device 108 of FIG. 1. Along with electrocardiographic and thoracic volume change signal recordings, the data may be used to develop a sleep efficiency prediction model that may project a sleep efficiency score based on PPG data (e.g., without requiring ECG data and thoracic volume data). The regression model, established using the ratio of the power of the low- and high-frequency bands of the heart rate variability signal of FIG. 2C and the average peak inspiratory flow value of FIG. 2B, may provide an absolute error (mean±SD) and a Pearson's correlation coefficient between the sleep efficiency predictive values and the reference values. With a combination of PPG data and device motion data, the model may determine a projected sleep efficiency and recommendations to improve sleep efficiency.

Figure 3A:
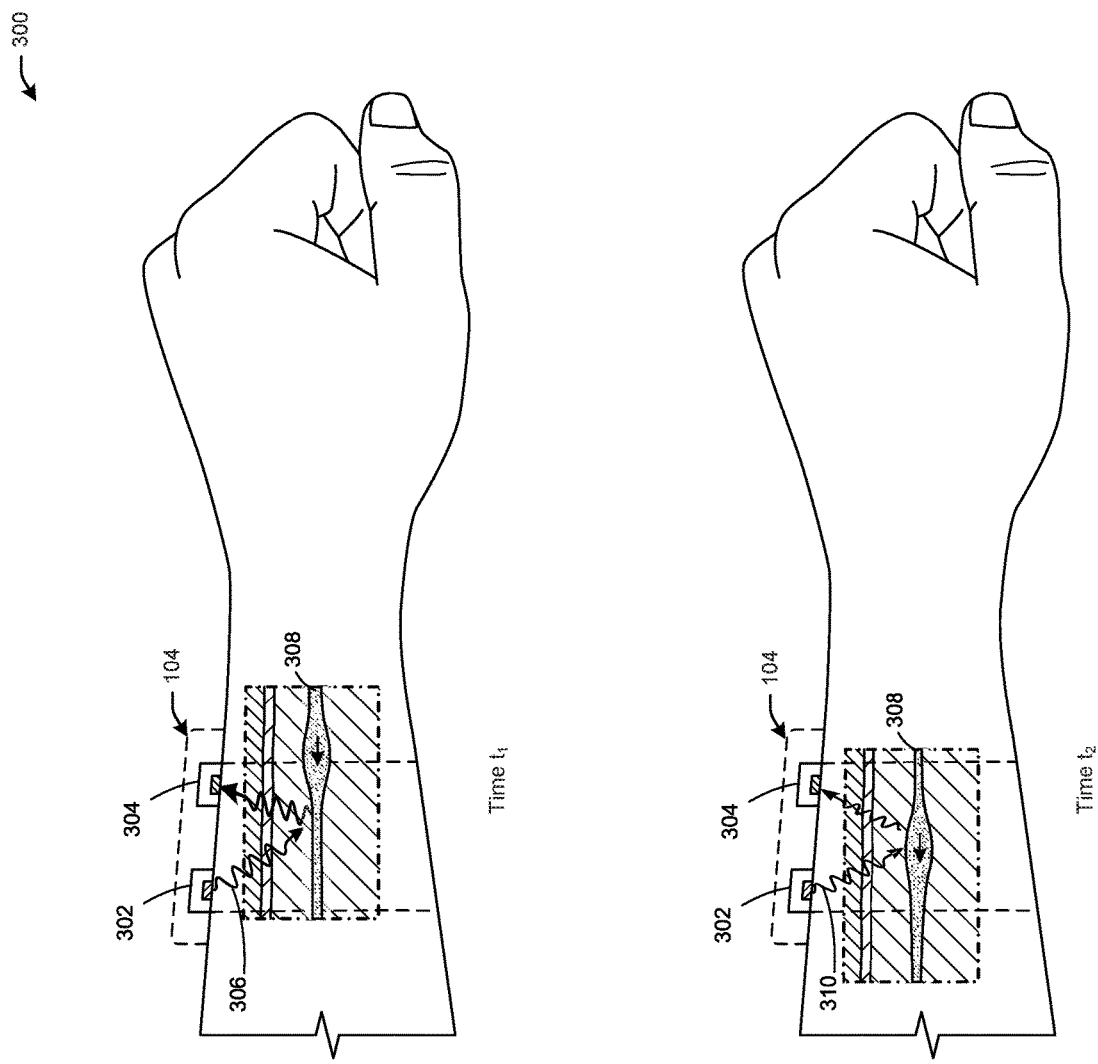
FIG. 3A illustrates an example system for measuring heart data using photoplethysmography, in accordance with one or more example embodiments of the present disclosure.

FIG. 3A illustrates an example system 300 for measuring heart data using PPG, in accordance with one or more example embodiments of the present disclosure.

Referring to FIG. 3A, the device 104 of FIG. 1 is shown as a wearable device with an emitter 302 and a detector 304. The emitter 302 may emit a light wave 306, which may propagate through a person's body and may reflect off of a blood vessel 308. The reflected light wave may be received by the detector 304, and may represent a rate of blood flow. At time $t_1$ (e.g., corresponding to the time $t_1$ of FIG. 2A), the blood flow may be represented by the PPG data 200 and the ECG data 220 of FIG. 2A (e.g., just before a PQRST wave). At time $t_2$ (e.g., corresponding to the time $t_2$ of FIG. 2A), the emitter 302 may emit a light wave 310, which may reflect off of the blood vessel 308, and the blood flow may be represented by the PPG data 200 and the ECG data 220 of FIG. 2A (e.g., during a PQRST wave). In this manner, the PPG data 200 and the ECG data 220 of FIG. 2A may represent heart data at different times.

In one or more embodiments, while the emitter 302 and the detector 304 are shown as separate devices (e.g., separate photodiodes), the emitter 302 and the detector 304 may be combined into one device (e.g., a single photodiode that emits and receives light). The separate emitter 302 and the detector 304 may be combined into one housing, for example.

Figure 3B:
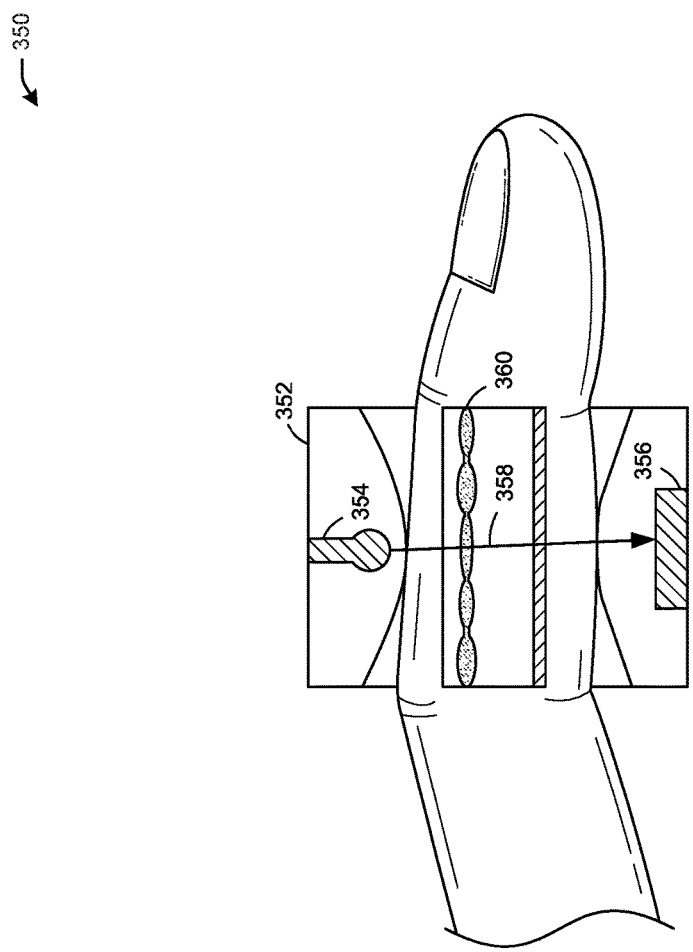
FIG. 3B illustrates an example system for measuring heart data using photoplethysmography, in accordance with one or more example embodiments of the present disclosure.

FIG. 3B illustrates an example system 350 for measuring heart data using PPG, in accordance with one or more example embodiments of the present disclosure.

Referring to FIG. 3B, the system 350 may use a transmission-based PPG method. For example, a device 352 (e.g., worn on a person's finger as shown) may include an emitter 354 and a detector 356 (e.g., photodiodes). The emitter 354 may emit a light wave 358 that may pass through a blood vessel 360, resulting in PPG data (e.g., as shown in FIG. 2A).

Figure 4:
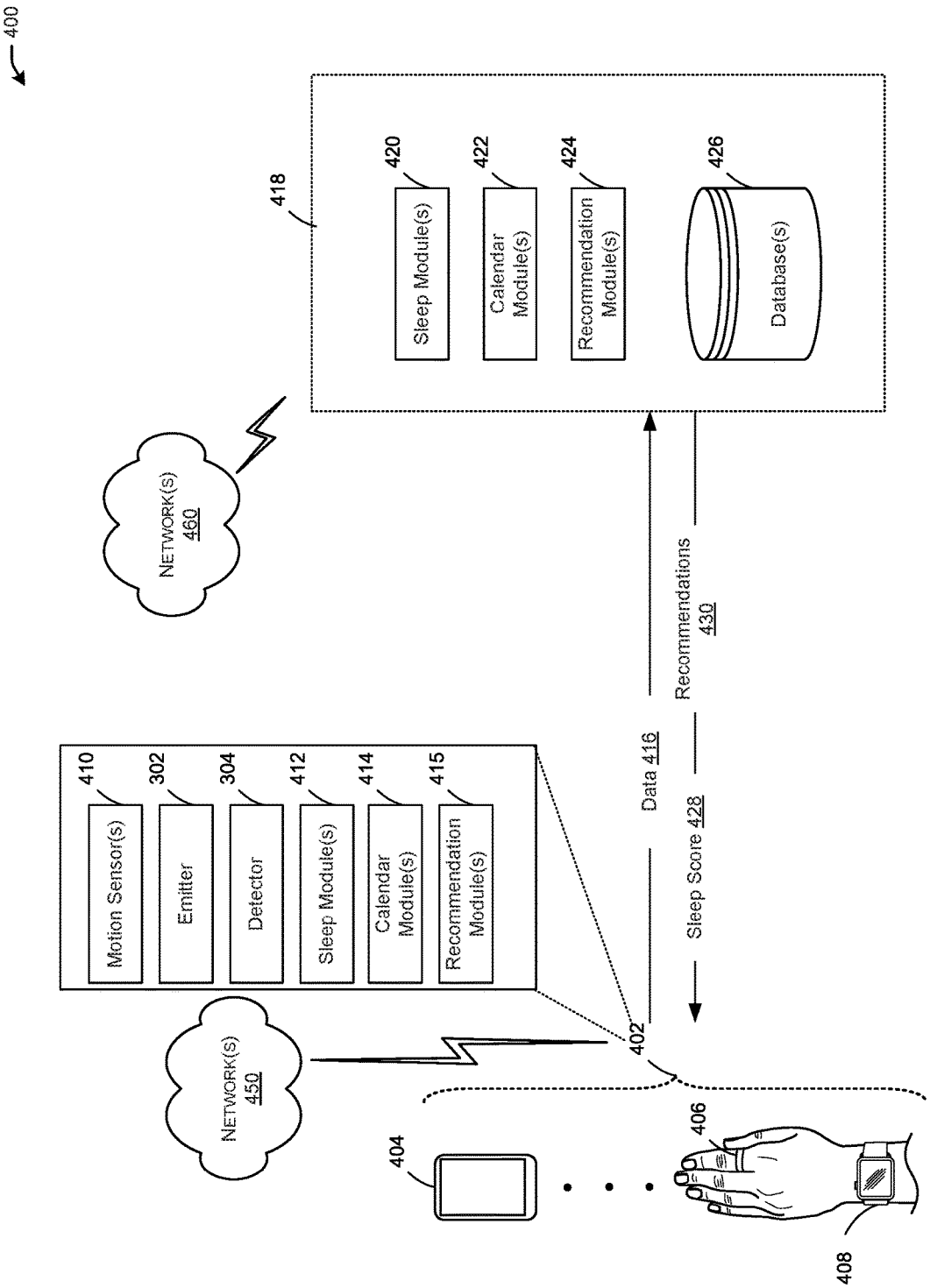
FIG. 4 illustrates an example system for sleep efficiency evaluations and recommendations, in accordance with one or more example embodiments of the present disclosure.

FIG. 4 illustrates an example system 400 for sleep efficiency evaluations and recommendations, in accordance with one or more example embodiments of the present disclosure.

Referring to FIG. 4, the system 400 may include one or more devices 402 (e.g., device 404, device 406, and device 408 similar to the device 104, the device 105, the device 106, the device 107, and the device 108 of FIG. 1). The one or more devices 402 may include one or more motion sensors 410 (e.g., accelerometers, magnetometers, global navigation/location sensors, etc.), the emitter 302 of FIG. 3A, the detector 304 of FIG. 3A, the emitter 354 of FIG. 3B, the detector 356 of FIG. 3B, one or more sleep modules 412, one or more calendar modules 414, and/or one or more recommendation modules 415. The one or more devices 402 may detect data 416 (e.g., device motion data, biometric data such as the heart data 150 of FIG. 1, body temperature data, etc.), and the one or more sleep modules 412 may determine a sleep efficiency score. The one or more recommendation modules 415 may determine one or more recommendations regarding activities to perform or not perform, food or beverage to consume or not consume, bed times, wake times, and the like to display using the one or more devices 402. The one or more calendar modules 414 may provide calendar/schedule information, such as upcoming events, travel plans, and the like, allowing the one or more recommendation modules 415 to determine recommended bed times, wake times, and activities.

Still referring to FIG. 4, the one or more devices 402 may send the data 416 to a network 418 (e.g., a cloud-based network). The network 418 may include one or more sleep modules 420 (e.g., similar to the one or more sleep modules 412), one or more calendar modules 422 (e.g., similar to the one or more calendar modules 414), one or more recommendation modules 424 (e.g., similar to the one or more recommendation modules 415), and one or more databases 426 (e.g., to store the data 416 and/or other activity and biometric data, such as the ECG data 220 of FIG. 2A, breathing data, activity data, consumption data, bed time data, wake time data, and the like). The network 418 may determine a sleep score 428 using the one or more sleep modules 420, and may determine one or more recommendations 430 using the one or more recommendation modules 424 (e.g., the data shown as displayed using the device 108 of FIG. 1). For example, consumption data may be determined automatically (e.g., using swallow/chewing detection based on sounds and/or images captured by the one or more devices 402), by user inputs/self-annotation (e.g., user inputs indicating what the user consumed), and/or by purchase data, grocery lists, or the like.

In one or more embodiments, the one or more sleep modules 412 or the one or more sleep modules 420 may include a machine-learning model that may determine a correlation between PPG data and sleep stages (e.g., early sleep, deep sleep, etc.). For example, a combination of PPG data, ECG data, HRV data, respiratory data, and device motion data may be used by the one or more sleep modules 412 or the one or more sleep modules 420 to determine an estimated sleep efficiency, and based on the estimated sleep efficiency, a sleep stage. For example, sleep stage classifiers (e.g., machine learning or deep learning models used by the one or more sleep modules 412 or the one or more sleep modules 420) may receive HRV metrics and device motion data as inputs, and may predict sleep stages (e.g., wake, light, deep, REM). Using the estimated sleep efficiency, the one or more sleep modules 412 or the one or more sleep modules 420 may determine when a person is likely to enter a particular sleep stage.

In one or more embodiments, the one or more sleep modules 412 or the one or more sleep modules 420 may determine a correlation between PPG data and sleep efficiency. For example, a LF/HF ratio and/or PIF may be indicative of a sleep stage or sleep efficiency. In addition, device motion data may correlate to activities (e.g., exercise, sedentary time, food consumption, etc.), and the one or more sleep modules 412 or the one or more sleep modules 420 may determine that, based on an amount and/or type of activity that a person has performed in a given time period (e.g., a current calendar day), the effects that the activity may have on sleep efficiency. For example, when past data for a user indicates that an amount and/or type of activity corresponds to an increase or decrease in sleep efficiency, the one or more sleep modules 412 or the one or more sleep modules 420 may predict a sleep efficiency based on the PPG data and the activity data. In particular, when an hour of exercise has resulted in the person's sleep score improving when compared to days when the person did not exercise, the one or more sleep modules 412 or the one or more sleep modules 420 may determine the person's sleep efficiency score based on whether or not the device motion data indicates that the person has exercised an hour (e.g., a threshold amount of time) that day. Different LF/HF ratios and/or PIFs determined based on PPG data by the one or more sleep modules 412 or the one or more sleep modules 420 may correspond to different sleep efficiency scores. For example, a LF/HF ratio within a range and/or a PIF ratio within a range may correspond to a sleep efficiency score. Exercise and/or consumption at a particular time range and/or within an amount of time range may correspond to an increase or decrease in sleep efficiency score that may be added to or subtracted from the score projected based on PPG data. The one or more sleep modules 412 or the one or more sleep modules 420 may project a sleep efficiency score based on a projected bed time and/or wake time.

In one or more embodiments, the one or more sleep modules 412 or the one or more sleep modules 420 may update a sleep model based on actual data. For example, the one or more sleep modules 412 or the one or more sleep modules 420 may determine the actual sleep efficiency score based on prior night's data, and may compare the actual data to the predicted score. When the predicted score is inaccurate, the one or more sleep modules 412 or the one or more sleep modules 420 may adjust the model by changing thresholds associated with LF/HF ratio ranges, PIF ranges, and/or activity amounts or times.

In one or more embodiments, the one or more recommendation modules 415 and/or the one or more recommendation modules 424 may determine recommended bed times, wake times, activities, meals, and the like. For example, the one or more recommendation modules 415 and/or the one or more recommendation modules 424 may determine a recommended bed time for a person based on a projected sleep efficiency score. When the sleep efficiency score is 80, and the recommended wake time (or a wake time based on an alarm set by a user) is 6:00 AM, then to achieve six hours of sleep may require the person's bed time to be 10:30 AM (e.g., a recommended bed time). Based on a person's normal bed time, the one or more recommendation modules 415 and/or the one or more recommendation modules 424 may recommend a wake time to allow the person to achieve a predicted sleep score. When the one or more calendar modules 414 and/or the one or more calendar modules 422 provide calendar data indicating that a person is traveling or has activities at a particular time, the one or more recommendation modules 415 and/or the one or more recommendation modules 424 may determine a recommended amount of sleep, a recommended bed time, and/or a recommended wake time to achieve a predicted sleep score. The one or more recommendation modules 415 and/or the one or more recommendation modules 424 may determine recommended activities and/or food/beverage based on past history, such as whether an activity, food, or beverage caused sleep efficiency to increase or decrease, whether the activity, food, or beverage caused a person to fall asleep earlier or later, whether the activity, food, or beverage caused a person to wake up earlier or later, and the like. For example, when the recommended bed time is 10:00 PM and the activity data indicates that the person is unlikely to fall asleep that early, the one or more recommendation modules 415 and/or the one or more recommendation modules 424 may recommend performance or non-performance of an activity that previously correlated to an earlier bed time, and/or may recommend consumption or non-consumption of food or beverage that previously correlated to an earlier bed time.

In one or more embodiments, the one or more devices 402 or the network 418 may receive heart signal data, such as PPG data (e.g., the PPG data 200 of FIG. 2A). Based on device motion data, the one or more devices 402 or the network 418 may determine a time period when the accelerometer data is below a motion threshold (e.g., indicative of a time when a person is relatively still—not sleeping, but awake). The time when the person is relatively still, the one or more devices 402 or the network 418 may determine the LF/HF ratio and the PIF (e.g., the PIF 272 of FIG. 2B) for that time period. The one or more devices 402 or the network 418 may determine a periodic duration of the PPG data (e.g., the period 212 of FIG. 2A, corresponding to a RR interval), the periodic duration occurring during the identified time period when the user was relatively still. The one or more devices 402 or the network 418 may identify a first portion of the PPG data in the frequency domain and during the time period that fails to exceed a threshold (e.g., the LF portion 282 below the threshold 284 of FIG. 2C) and may identify a second portion of the PPG data in the frequency domain that exceeds the threshold (e.g., the HF portion 286 exceeding the threshold 284 of FIG. 2C). Based on the first and second portions in the frequency domain, the one or more devices 402 or the network 418 may determine the LF/HF ratio as a HRV metric. Based on the PPG data, the one or more devices 402 or the network 418 may determine a respiration rate (e.g., a rate at which a person is breathing as measured by the period 260 when a person is inhaling and the period 270 when the person is exhaling, as shown in FIG. 2B). For example, the time it takes to complete the period 260 and the period 270 may represent a respiration cycle. The number of respiration cycles per unit time may represent a respiration rate. Based on the respiration rate, the PIF 272 may be determined. Based on the LF/HF ratio and the PIF for the time period, the one or more devices 402 or the network 418 may determine a forecasted sleep efficiency score for a person. Based on the device motion data, the one or more devices 402 or the network 418 may determine a recommended activity to improve or achieve the forecasted sleep efficiency score, and may present the forecasted sleep efficiency score, recommended activity, and effects of the recommended activity on the forecasted sleep efficiency score. In this manner, heart data and other data may be analyzed in real-time to forecast a person's sleep efficiency score, and to recommend performance or non-performance of activities to affect the sleep efficiency score.

The one or more devices 402 may be configured to communicate via a communications network 450, and the network 418 may be configured to communicate via the communications network 460, wirelessly or wired (e.g., the same or different wireless communications networks). The communications network 450, and/or the communications network 460 may include, but not limited to, any one of a combination of different types of suitable communications networks such as, for example, broadcasting networks, cable networks, public networks (e.g., the Internet), private networks, wireless networks, cellular networks, or any other suitable private and/or public networks. Further, the communications network 450, and/or the communications network 460 may have any suitable communication range associated therewith and may include, for example, global networks (e.g., the Internet), metropolitan area networks (MANs), wide area networks (WANs), local area networks (LANs), or personal area networks (PANs). In addition, communications network 450 and/or the communications network 460 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, white space communication mediums, ultra-high frequency communication mediums, satellite communication mediums, or any combination thereof.

The one or more devices 402 and/or the network 418 may include any suitable processor-driven device including, but not limited to, a mobile device or a non-mobile, e.g., a static, device. For example, one or more devices 402 and/or the network 418 may include a user equipment (UE), a station (STA), an access point (AP), a personal computer (PC), a wearable wireless device (e.g., bracelet, watch, glasses, ring, etc.), a desktop computer, a mobile computer, a laptop computer, an Ultrabook™ computer, a notebook computer, a tablet computer, a server computer, a handheld computer, a handheld device, an internet of things (IoT) device, a sensor device, a PDA device, a handheld PDA device, an on-board device, an off-board device, a hybrid device (e.g., combining cellular phone functionalities with PDA device functionalities), a consumer device, a vehicular device, a non-vehicular device, a mobile or portable device, a non-mobile or non-portable device, a mobile phone, a cellular telephone, a PCS device, a PDA device which incorporates a wireless communication device, a mobile or portable GPS device, a DVB device, a relatively small computing device, a non-desktop computer, a "carry small live large" (CSLL) device, an ultra mobile device (UMD), an ultra mobile PC (UMPC), a mobile internet device (MID), an "origami" device or computing device, a device that supports dynamically composable computing (DCC), a context-aware device, a video device, an audio device, an A/V device, or the like. It is understood that the above is a list of devices. However, other devices may also be included in this list.

Figure 5A:
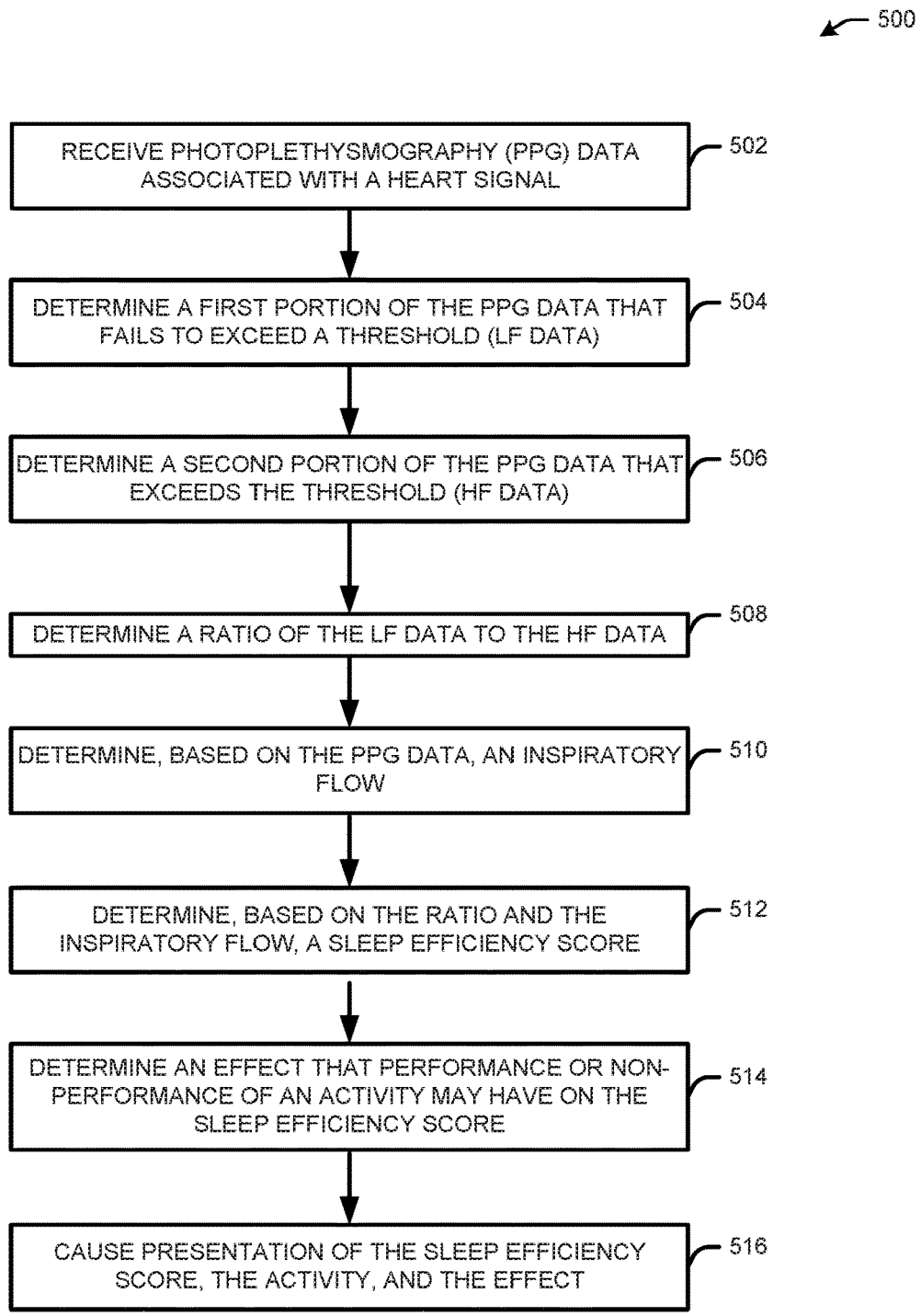
FIG. 5A illustrates a flow diagram for a process for performing sleep efficiency evaluations and recommendations, in accordance with one or more example embodiments of the present disclosure.

FIG. 5A illustrates a flow diagram for a process 500 for performing sleep efficiency evaluations and recommendations, in accordance with one or more example embodiments of the present disclosure.

At block 502, a system (e.g., the device 104 of FIG. 1, the device 105, the device 106 of FIG. 1, the device 107, the device 108 of FIG. 1, the one or more devices 402 of FIG. 4, the network 418 of FIG. 4) may receive PPG data (e.g., the PPG data 200 of FIG. 2A) associated with a heart signal (e.g., represented by the blood vessel 308 blood flow of FIG. 3). The PPG data may include multiple periodic intervals of the same and/or varying length in time (e.g., the data periods 212-218 of FIG. 2A). The PPG data may be detected non-invasively (e.g., using the emitter 302 and the detector 304 of FIG. 3A, or the emitter 354 and the detector 356 of FIG. 3B).

At block 504, the system may determine a first portion of the PPG data that fails to exceed a threshold (e.g., the portion 282 of FIG. 2C below the threshold frequency 284). The system may evaluate the PPG data in the frequency domain and may determine the low-frequency (LF) portion, which may be between 0.04 and 0.15 Hz. The system may measure the power of the PPG data (e.g., heart signal) that falls within the low-threshold frequency range. The first portion may be considered a HRV metric.

At block 506, the system may determine a second portion of the PPG data that exceeds the threshold (e.g., the portion 286 of FIG. 2C above the threshold frequency 284). The system may evaluate the PPG data in the frequency domain and may determine the high-frequency (HF) portion, which may be between 0.15 and 0.4 Hz. The system may measure the power of the PPG data (e.g., heart signal) that falls within the high-threshold frequency range. The second portion may be considered a HRV metric. At block 508, the system may determine a ratio of the first and second portions (e.g., the LF/HF ratio as a HRV metric). Unlike some systems, the system may determine the LF and HF portions of a PPG signal rather than requiring ECG data.

At block 510, the system may determine, based on the PPG data, an inspiratory flow (e.g., the PIF 272 of FIG. 2B). Using the periods of the PPG data (e.g., corresponding to RR intervals or any other intervals represented by repeating PPG data over time), the system may identify the times when a person is inhaling and exhaling. Based on the person's inspiratory times, the system may identify the PIF. In this manner, the system may correlate the PIF to the PPG data rather than requiring an invasive technique to collect breathing data.

At block 512, based on the LF/HF ratio and the PIF, the system may determine one or more sleep efficiency scores, such as an actual sleep efficiency based on a previous time (e.g., when the person was asleep) or a forecasted sleep efficiency score (e.g., for an upcoming sleep that has not yet occurred). For example, when the LF/HF ratio and the PIF indicate metrics for a person's heart and breathing during a day, the sleep efficiency score may be a sleep efficiency score for that night (e.g., the person will sleep efficiently or inefficiently based on behavior exhibited during the day or the person slept efficiently). The LF/HF ratio and PIF may correspond to sleep stages and sleep efficiency scores. For example, the LF/HF ratio and PIF may map to a sleep efficiency score and/or to one or more sleep stages. The system may consider past data indicating that the LF/HF ratio and the PIF at certain times and/or corresponding to certain activities performed by the person resulted in a past sleep efficiency score.

At block 514, the system may determine an effect that performance or non-performance of an activity may have on the person's sleep efficiency score. For example, when the person has exercised a certain amount of time in the past, the person may have had a higher sleep efficiency score than when the person exercised less than the amount of time. In this manner, the system may determine that exercising the amount of time may improve the forecasted sleep efficiency score, and that not exercising the amount of time may reduce the forecasted sleep efficiency score. In this manner, the system may determine whether certain activities may improve or reduce the forecasted sleep efficiency score so that the person may decide to perform or not perform actions accordingly. For example, a recommended activity may include a bed time and/or wake time, an amount and/or type of activity to perform or not perform, a food or beverage to consume or not consume, a time during which to perform or not perform an action (e.g., not to eat or exercise past a certain time, etc.), and the like. Performance of an activity may increase or decrease stress levels, and therefore HRV, indicating an improvement or detriment to a sleep efficiency score. In this manner, whether an activity corresponded in a change in heart rate and or breathing rate may be indicative of whether the activity improved a sleep activity score.

At block 516, the system may cause presentation of the forecasted sleep efficiency score, the activity, whether the activity is recommended or not, and/or the effect that performance of the activity may have on the person's sleep efficiency, and the like. The system may present the information on its own display, or may send the information to another device for presentation. An example of the presentation is shown in FIG. 1.

Figure 5B:
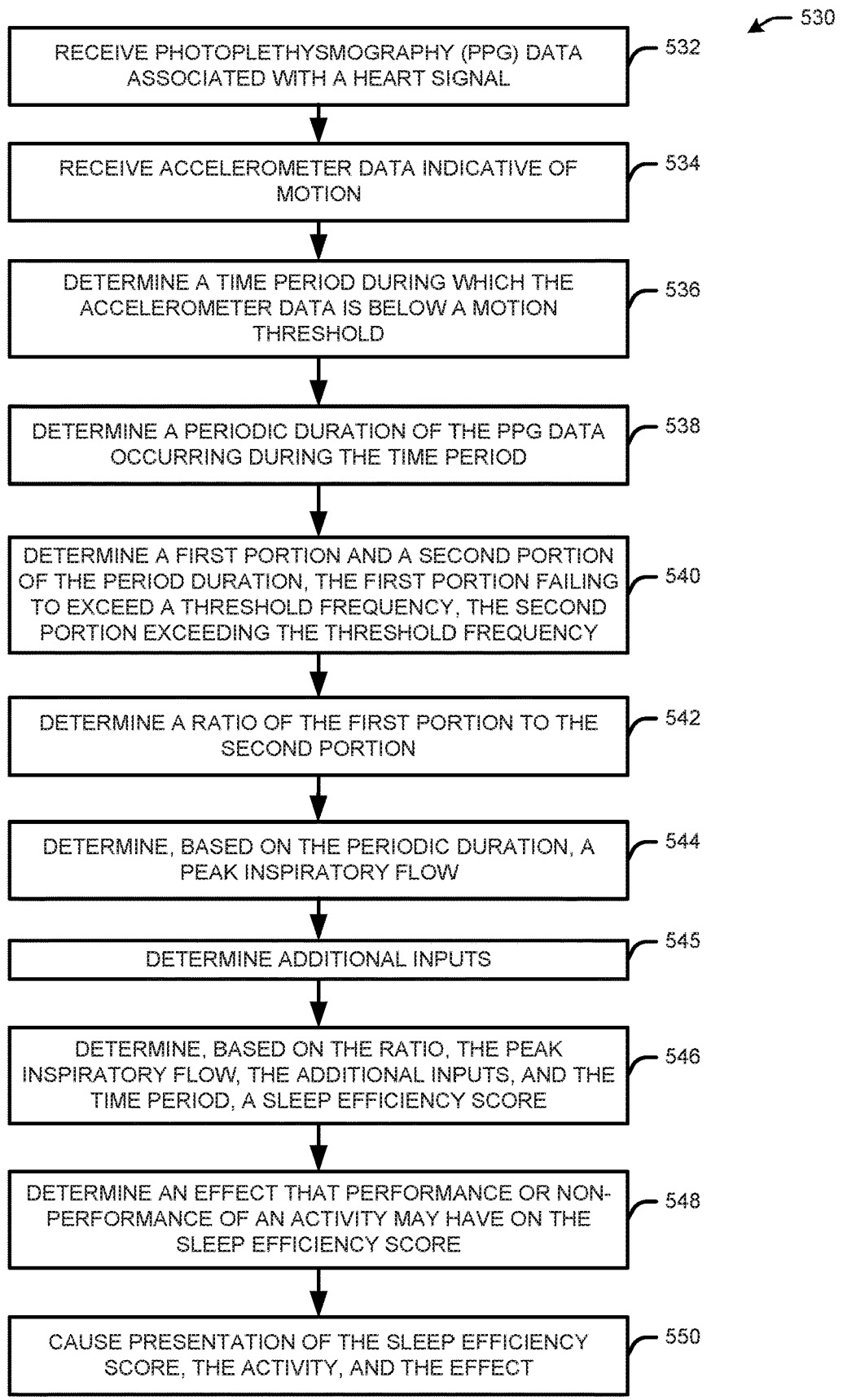
FIG. 5B illustrates a flow diagram for a process for performing sleep efficiency evaluations and recommendations, in accordance with one or more example embodiments of the present disclosure.

FIG. 5B illustrates a flow diagram for a process 530 for performing sleep efficiency evaluations and recommendations, in accordance with one or more example embodiments of the present disclosure.

At block 532, a system (e.g., the device 104 of FIG. 1, the device 106 of FIG. 1, the device 108 of FIG. 1, the one or more devices 402 of FIG. 4, the network 418 of FIG. 4) may receive PPG data (e.g., the PPG data 200 of FIG. 2A) associated with a heart signal (e.g., represented by the blood vessel 308 blood flow of FIG. 3A or the blood vessel 360 blood flow of FIG. 3B). The PPG data may include multiple periodic intervals of the same and/or varying length in time (e.g., the data periods 212-218 of FIG. 2A). The PPG data may be detected non-invasively (e.g., using the emitter 302 and the detector 304 of FIG. 3A, or the emitter 354 and the detector 356 of FIG. 3B).

At block 534, the system may receive accelerometer or other device motion data indicative of motion. For example, the system may include a multi-dimensional accelerometer, and may determine, using the accelerometer data, that the device (e.g., and therefore a device user) is moving. The system may determine when the device user may be sleeping or otherwise sedentary (e.g., when the accelerometer is at or near zero). In this manner, the system may use accelerometer data to identify times when a device user is relatively still (e.g., relatively inactive, but not necessarily asleep), and evaluate data during that time to forecast a sleep efficiency score (e.g., contrasted with determining when a person actually was asleep and what the person's actual sleep efficiency score is, which the system also may do). For example, at block 536, the system may determine a period of time when the accelerometer data is below a motion threshold. Low motion indicated by the accelerometer data may indicate that the person is relatively still.

At block 538, using the period of time when the person is relatively still, the system may determine a periodic duration (e.g., the data periods 212-218 of FIG. 2A) of the PPG data. The system may determine a time period during the day when the person is relatively still, as indicated by the accelerometer data, and may evaluate PPG data during that time period. Based on the PPG data during that time period, the system may identify periodic portions of PPG data (e.g., corresponding to RR intervals or any other like data points that repeat periodically). Using the repeating periods of PPG data, the system may determine HRV and respiratory metrics used to forecast a sleep efficiency score (e.g., without requiring the corresponding ECG data for the time period, and/or without requiring invasive measurements).

At block 540, the system may determine a first portion of the PPG data that fails to exceed a threshold (e.g., the portion 282 of FIG. 2C below the threshold frequency 284). The system may evaluate the PPG data in the frequency domain and may determine the low-frequency (LF) portion, which may be between 0.04 and 0.15 Hz. The system may measure the power of the PPG data (e.g., heart signal) that falls within the low-threshold frequency range. The first portion may be considered a HRV metric. Similarly, the system may determine a second portion of the PPG data that exceeds the threshold (e.g., the portion 286 of FIG. 2C above the threshold frequency 284). The system may evaluate the PPG data in the frequency domain and may determine the high-frequency (HF) portion, which may be between 0.15 and 0.4 Hz. The system may measure the power of the PPG data (e.g., heart signal) that falls within the high-threshold frequency range. The second portion may be considered a HRV metric. At block 542, the system may determine a ratio of the first and second portions (e.g., the LF/HF ratio as a HRV metric). Unlike some systems, the system may determine the LF and HF portions of a PPG signal rather than requiring ECG data.

At block 544, the system may determine, based on the periodic duration of the PPG data, a PIF (e.g., the PIF 272 of FIG. 2B). Using the periods of the PPG data (e.g., corresponding to RR intervals or any other intervals represented by repeating PPG data over time), the system may identify the times when a person is inhaling and exhaling. Based on the person's inspiratory times, the system may identify the PIF. In this manner, the system may correlate the PIF to the PPG data rather than requiring an invasive technique to collect breathing data. Heart rate generally increases during inhalation and decreases during exhalation. Relatedly, the periodic duration may be shorter during inspiration and longer during expiration. In this manner, longer periodic duration may be indicative of expiration, and shorter periodic duration may be indicative of inhalation, allowing for an identification of a person's respiration rate by identifying how often the person is inhaling and exhaling during a period of time. As such, the PIF may be based on the periodic duration.

At block 545, the system may determine additional inputs (e.g., additional to the PPG data and device motion data). The additional inputs may be indicative of a person's stress levels or energy exerted. For example, voice data (e.g., a person's tone of voice, volume, or word speed) may indicate whether a person is stressed and/or has exerted energy. In this manner, voice data or other data indicative of a person's stress or energy level may be considered when evaluating sleep efficiency because, as explained above, stress and energy may correspond to variations in breathing and heart beats.

At block 546, the system may determine a forecasted sleep efficiency score based on the LF/HF ratio, the PIF, the additional inputs, and the time period. For example, when the LF/HF ratio and the PIF indicate metrics for a person's heart and breathing during a day, the forecasted sleep efficiency score may be a projected sleep efficiency score for that night (e.g., the person will sleep efficiently or inefficiently based on behavior exhibited during the day). The LF/HF ratio and PIF may correspond to sleep stages and sleep efficiency scores. For example, the LF/HF ratio and PIF may map to a sleep efficiency score and/or to one or more sleep stages. The system may consider past data indicating that the LF/HF ratio and the PIF at certain times and/or corresponding to certain activities performed by the person resulted in a past sleep efficiency score.

At block 548, the system may determine an effect that performance or non-performance of an activity may have on the person's sleep efficiency score. For example, when the person has exercised a certain amount of time in the past, the person may have had a higher sleep efficiency score than when the person exercised less than the amount of time. In this manner, the system may determine that exercising the amount of time may improve the forecasted sleep efficiency score, and that not exercising the amount of time may reduce the forecasted sleep efficiency score. In this manner, the system may determine whether certain activities may improve or reduce the forecasted sleep efficiency score so that the person may decide to perform or not perform actions accordingly. For example, a recommended activity may include a bed time and/or wake time, an amount and/or type of activity to perform or not perform, a food or beverage to consume or not consume, a time during which to perform or not perform an action (e.g., not to eat or exercise past a certain time, etc.), and the like.

At block 550, the system may cause presentation of the forecasted sleep efficiency score, the activity, whether the activity is recommended or not, and/or the effect that performance of the activity may have on the person's sleep efficiency, and the like. The system may present the information on its own display, or may send the information to another device for presentation. An example of the presentation is shown in FIG. 1.

Figure 5C:
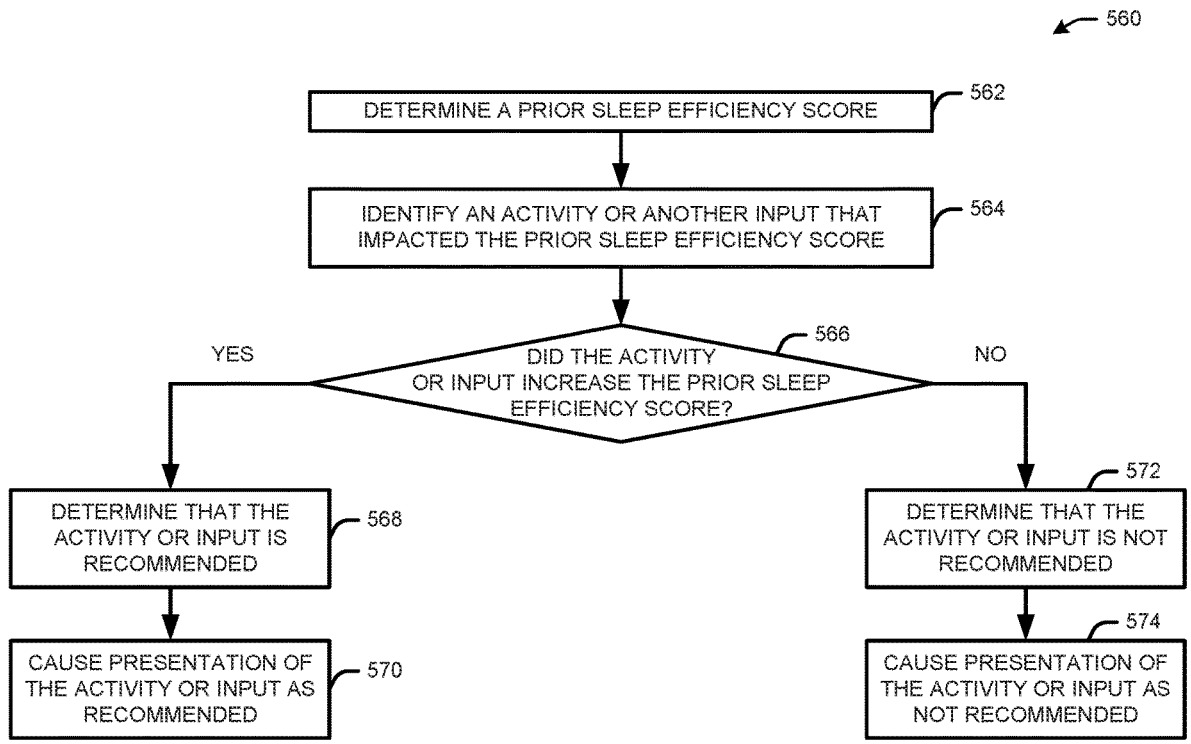
FIG. 5C illustrates a flow diagram for a process for performing sleep efficiency evaluations and recommendations, in accordance with one or more example embodiments of the present disclosure.

FIG. 5C illustrates a flow diagram for a process 560 for performing sleep efficiency evaluations and recommendations, in accordance with one or more example embodiments of the present disclosure.

At block 562, a system (e.g., the device 104 of FIG. 1, the device 106 of FIG. 1, the device 108 of FIG. 1, the one or more devices 402 of FIG. 4, the network 418 of FIG. 4) may determine a prior sleep efficiency score (e.g., an actual sleep efficiency score determined based on a person's past sleep efficiency). A model used by the system may forecast sleep efficiency scores and may compare actual sleep efficiency scores to the forecasted sleep efficiency scores. The system may update the model when the forecasts differ from the actual sleep efficiency scores. For example, the system may determine actions performed and/or not performed prior to the person sleeping, and may adjust the predictions of the model based on how significant the effects of an action may have been on the person's actual sleep efficiency (e.g., a determination that too much exercise resulted in a lower sleep efficiency than forecasted, a determination that consumption of food or beverage after a certain hour resulted in a lower sleep efficiency than forecasted, etc.).

At block 564, the system may identify an activity performed or not performed prior to the person's actual prior sleep score (e.g., within the day preceding the night for which the sleep score was determined). The system may identify another input, such as stress level, energy exertion, body temperature, and the like that may have affected the prior sleep efficiency score. The system may evaluate whether the performance or non-performance of the activity caused a higher or lower sleep efficiency score than projected. For example, a lack (e.g., non-performance) of exercise in a day may have led to a lower sleep efficiency score. Exercise for a threshold amount of time may have led to a higher sleep efficiency score. Change in body temperature (e.g., due to physical exertion) may affect HRV and/or breathing, and therefore may affect sleep efficiency. Change in stress level (e.g., as indicated by voice or activity data) may affect HRV and/or breathing, and therefore may affect sleep efficiency.

At block 566, the system may determine whether the activity or other input increased the prior sleep efficiency score or whether the activity is known to correlate with higher sleep efficiency scores (e.g., based on historical data of the user and/or other users). When the activity or other input is known to increase the sleep efficiency score, the system may determine, at block 568, that the activity or other input is recommended and its effect on the sleep efficiency score (e.g., an increase of X sleep efficiency points). At block 570, the system may cause presentation (e.g., using its own display or by sending data to another device for presentation) of an indication that the activity or other input is recommended. The presentation may indicate the anticipated effect of performance on the sleep efficiency score (e.g., "If you perform activity X, your sleep efficiency score may be Y"). When the system determines, at block 566, that the activity or other input does not increase sleep efficiency, the system may, at block 572, determine that the activity or other input is not recommended, and the impact that performance of the activity or other input may have on the sleep efficiency score (e.g., a decrease of X sleep efficiency points). At block 574, the system may cause presentation (e.g., using its own display or by sending data to another device for presentation) of an indication that the activity or other input is not recommended. The presentation may indicate the anticipated effect of performance on the sleep efficiency score (e.g., "If you perform activity X, your sleep efficiency score may be Y").

Figure 5D:
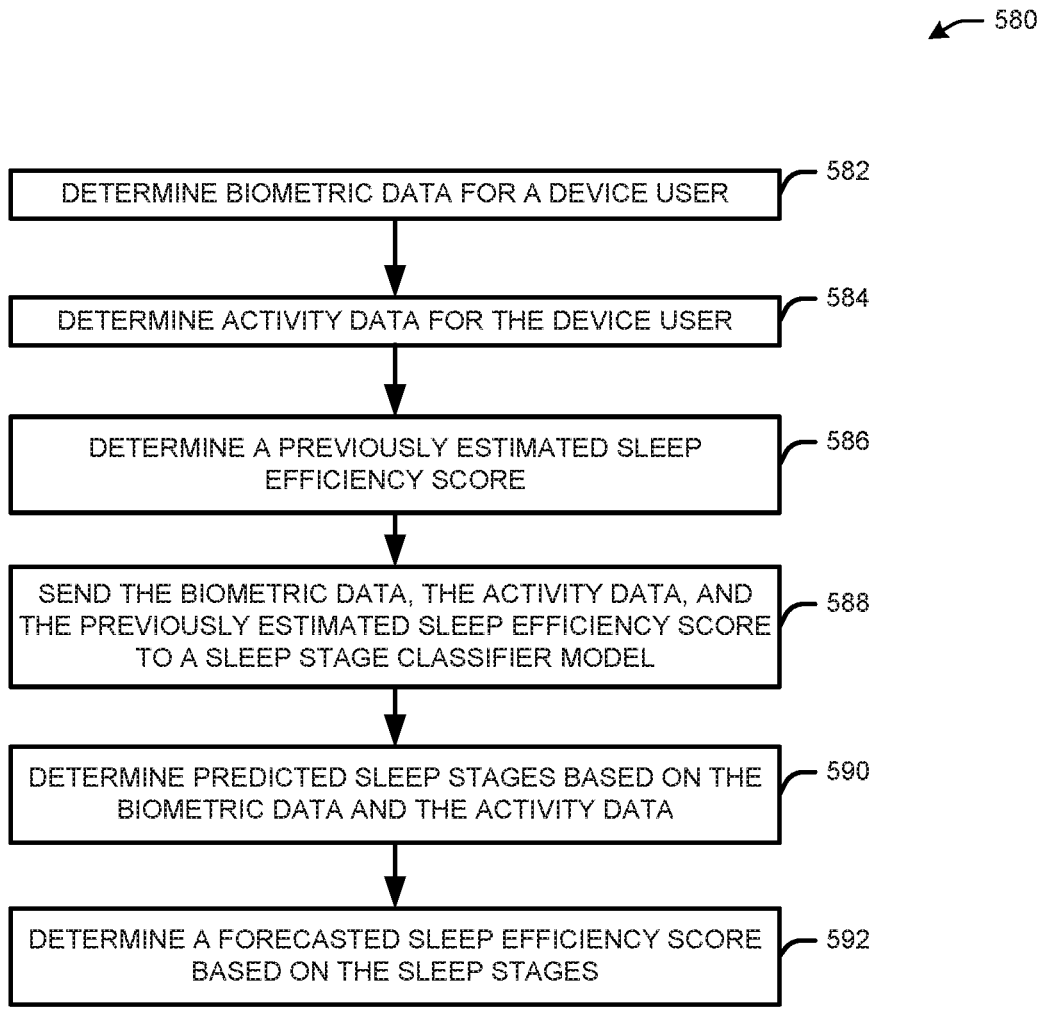
FIG. 5D illustrates a flow diagram for a process for performing sleep efficiency evaluations and recommendations, in accordance with one or more example embodiments of the present disclosure.

FIG. 5D illustrates a flow diagram for a process 580 for performing sleep efficiency evaluations and recommendations, in accordance with one or more example embodiments of the present disclosure.

At block 582, a system (e.g., the device 104 of FIG. 1, the device 106 of FIG. 1, the device 108 of FIG. 1, the one or more devices 402 of FIG. 4, the network 418 of FIG. 4) may determine biometric data for a device user. Biometric data, such as heart rate (HR), breathing rate, pulse oximetry, body fat, hydration level, body temperature, blood sugar, and the like, may indicate whether a person is sleeping, sedentary, or active. The combination of device and biometric data may provide indications of activity levels of a person over a period of time, and may correspond to HRV metrics and breathing rate. For example, a change in body temperature may indicate stress or physical exertion, corresponding to a change in breathing or heart rate, and therefore affecting a sleep efficiency score.

At block 584, the system may determine activity data for the device user. For example, the system may include a multi-dimensional accelerometer, and may determine, using the accelerometer data, that the device (e.g., and therefore a device user) is moving. The system may determine when the device user may be sleeping or otherwise sedentary (e.g., when the accelerometer is at or near zero). In this manner, the system may use accelerometer data to identify times when a device user is relatively still (e.g., relatively inactive, but not necessarily asleep), and evaluate data during that time to forecast a sleep efficiency score (e.g., contrasted with determining when a person actually was asleep and what the person's actual sleep efficiency score is, which the system also may do). For example, at block 536, the system may determine a period of time when the accelerometer data is below a motion threshold. Low motion indicated by the accelerometer data may indicate that the person is relatively still. Other activity data may include food/beverage consumption, which may be detected automatically or based on user inputs.

At block 586, the system may determine a prior sleep efficiency score (e.g., an actual sleep efficiency score determined based on a person's past sleep efficiency). A model used by the system may forecast sleep efficiency scores and may compare actual sleep efficiency scores to the forecasted sleep efficiency scores. The system may update the model when the forecasts differ from the actual sleep efficiency scores.

At block 588, the system may send the biometric data, the activity data, and the previously estimated sleep efficiency score to a sleep stage classifier model of the system (e.g., the one or more sleep modules 420 of FIG. 4). The sleep stage classifier model may be a machine learning or deep learning model on a same device as or different device from the system.

At block 590, the system may, using the sleep stage classifier model, determine predicted sleep stages (e.g., wake, light, deep, REM) based on the biometric data, the activity data, and the previously estimated sleep efficiency score. For example, when the system determines that the biometric data and/or activity data that were used to determine the previously estimated sleep efficiency score are the same as or similar to (e.g., within threshold values of) biometric data and/or activity data being used to forecast an upcoming sleep efficiency score, the system may determine whether predicted sleep stages were accurate (e.g., times for the stages). When the sleep stages were accurate (e.g., within threshold times from) the actual sleep stages determined for the person, the system may determine a sleep efficiency score that may be the same or similar to the previously estimated sleep efficiency score. When the previous estimates of sleep stages were not within threshold times of the actual sleep stages, the system may adjust the model and forecast sleep stages based on updated relationships between the biometric data and/or activity data and sleep stages.

At block 592, the system may determine a forecasted sleep efficiency score based on the sleep stages. For example, based on the times of sleep stages, the system may determine sleep efficiency. Using previous sleep efficiency scores and their associated sleep stage times, the system may determine the relationships between different sleep stages and sleep efficiency. Based on the projected sleep stages and their identified relationships with sleep efficiency, the system may predict a sleep efficiency score.

The descriptions herein are not meant to be limiting.

Figure 6:
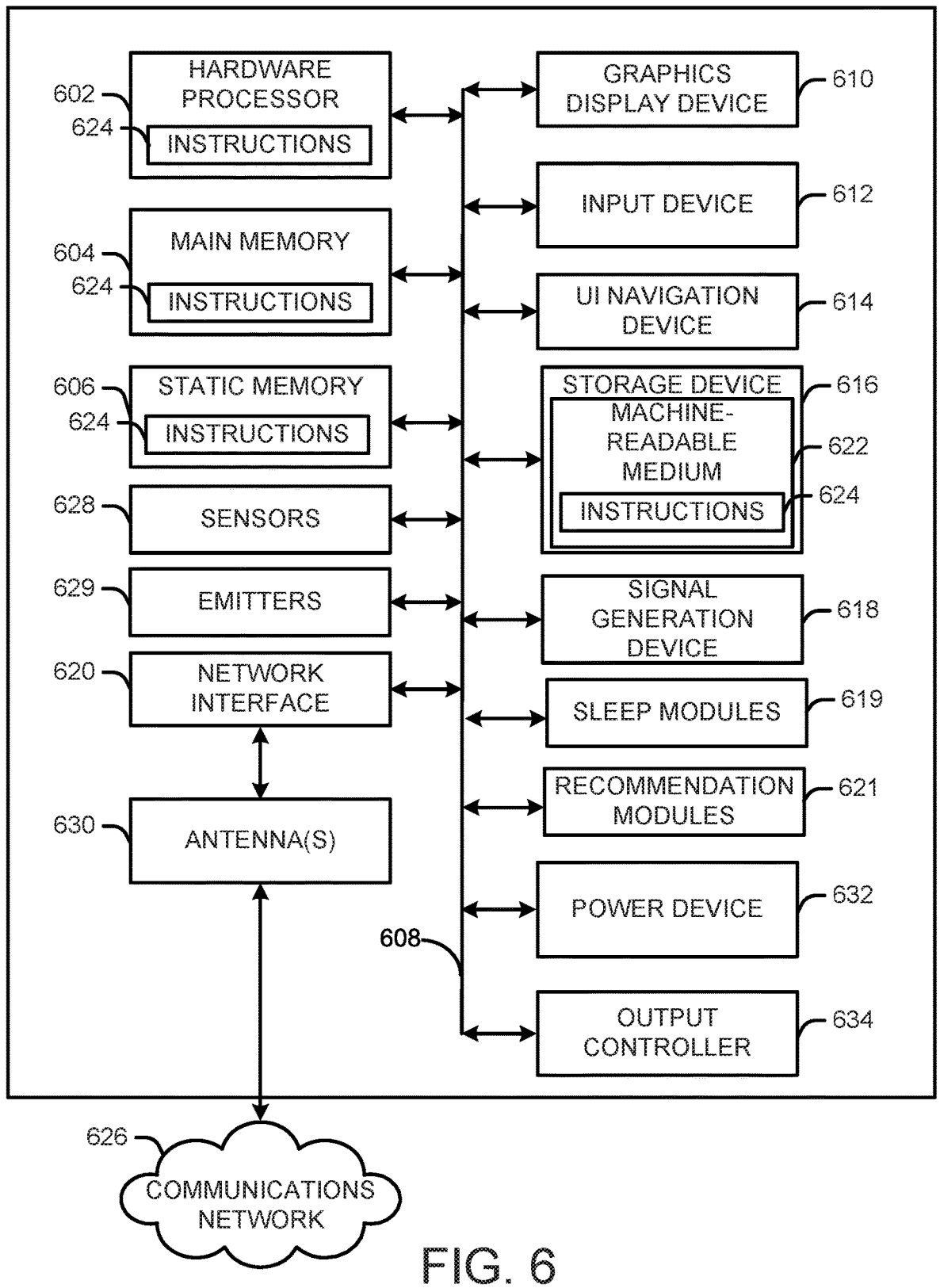
FIG. 6 illustrates a block diagram of an example machine upon which any of one or more techniques (e.g., methods) may be performed, in accordance with one or more example embodiments of the present disclosure.

FIG. 6 illustrates a block diagram of an example of a machine 600 (e.g., the device 104 of FIG. 1, the device 106 of FIG. 1, the device 108 of FIG. 1, the one or more devices 402 of FIG. 4, the network 418 of FIG. 4) or system upon which any one or more of the techniques (e.g., methodologies) discussed herein may be performed. In other embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in Wi-Fi direct, peer-to-peer (P2P), cellular, (or other distributed) network environments. The machine 600 may be a server, a personal computer (PC), a smart home device, a tablet PC, a set-top box (STB), a personal digital assistant (PDA), a mobile telephone, a wearable computer device, a web appliance, a network router, a switch or bridge, or any machine capable of executing instructions (sequential or otherwise) that specify actions to be taken by that machine, such as a base station. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), or other computer cluster configurations.

Examples, as described herein, may include or may operate on logic or a number of components, modules, or mechanisms. Modules are tangible entities (e.g., hardware) capable of performing specified operations when operating. A module includes hardware. In an example, the hardware may be specifically configured to carry out a specific operation (e.g., hardwired). In another example, the hardware may include configurable execution units (e.g., transistors, circuits, etc.) and a computer readable medium containing instructions where the instructions configure the execution units to carry out a specific operation when in operation. The configuring may occur under the direction of the executions units or a loading mechanism. Accordingly, the execution units are communicatively coupled to the computer-readable medium when the device is operating. In this example, the execution units may be a member of more than one module. For example, under operation, the execution units may be configured by a first set of instructions to implement a first module at one point in time and reconfigured by a second set of instructions to implement a second module at a second point in time.

The machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a power management device 632, a graphics display device 610, an alphanumeric input device 612 (e.g., a keyboard), and a user interface (UI) navigation device 614 (e.g., a mouse). In an example, the graphics display device 610, alphanumeric input device 612, and UI navigation device 614 may be a touch screen display. The machine 600 may additionally include a storage device (i.e., drive unit) 616, a signal generation device 618, one or more sleep modules 619 (e.g., similar to the one or more sleep modules 412 and/or the one or more sleep modules 420 of FIG. 4), a network interface device/transceiver 620 coupled to antenna(s) 630, one or more recommendation modules (e.g., similar to the one or more recommendation modules 415 and/or the one or more recommendation modules 424 of FIG. 4), one or more sensors 628, such as the detector 304 of FIG. 3A or the detector 356 of FIG. 3B, a microphone, a global positioning system (GPS) sensor, a compass, an accelerometer, or other sensor, and one or more emitters 629 (e.g., similar to the emitter 302 of FIG. 3 or the emitter 354 of FIG. 3B). The machine 600 may include an output controller 634, such as a serial (e.g., universal serial bus (USB), parallel, or other wired or wireless (e.g., infrared (IR), near field communication (NFC), etc.) connection to communicate with or control one or more peripheral devices (e.g., a printer, a card reader, etc.)).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within the static memory 606, or within the hardware processor 602 during execution thereof by the machine 600. In an example, one or any combination of the hardware processor 602, the main memory 604, the static memory 606, or the storage device 616 may constitute machine-readable media.

While the machine-readable medium 622 is illustrated as a single medium, the term "machine-readable medium" may include a single medium or multiple media (e.g., a centralized or distributed database, and/or associated caches and servers) configured to store the one or more instructions 624.

Various embodiments may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "machine-readable medium" may include any medium that is capable of storing, encoding, or carrying instructions for execution by the machine 600 and that cause the machine 600 to perform any one or more of the techniques of the present disclosure, or that is capable of storing, encoding, or carrying data structures used by or associated with such instructions. Non-limiting machine-readable medium examples may include solid-state memories and optical and magnetic media. In an example, a massed machine-readable medium includes a machine-readable medium with a plurality of particles having resting mass. Specific examples of massed machine-readable media may include non-volatile memory, such as semiconductor memory devices (e.g., electrically programmable read-only memory (EPROM), or electrically erasable programmable read-only memory (EEPROM)) and flash memory devices; magnetic disks, such as internal hard disks and removable disks; magneto-optical disks; and CD-ROM and DVD-ROM disks.

The instructions 624 may further be transmitted or received over a communications network 626 using a transmission medium via the network interface device/transceiver 620 utilizing any one of a number of transfer protocols (e.g., frame relay, internet protocol (IP), transmission control protocol (TCP), user datagram protocol (UDP), hypertext transfer protocol (HTTP), etc.). Example communications networks may include a local area network (LAN), a wide area network (WAN), a packet data network (e.g., the Internet), mobile telephone networks (e.g., cellular networks), plain old telephone (POTS) networks, wireless data networks (e.g., Institute of Electrical and Electronics Engineers (IEEE) 602.11 family of standards known as Wi-Fi®, IEEE 602.16 family of standards known as WiMax®), IEEE 602.15.4 family of standards, and peer-to-peer (P2P) networks, among others. In an example, the network interface device/transceiver 620 may include one or more physical jacks (e.g., Ethernet, coaxial, or phone jacks) or one or more antennas to connect to the communications network 626. In an example, the network interface device/transceiver 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding, or carrying instructions for execution by the machine 600 and includes digital or analog communications signals or other intangible media to facilitate communication of such software.

The operations and processes described and shown above may be carried out or performed in any suitable order as desired in various implementations. Additionally, in certain implementations, at least a portion of the operations may be carried out in parallel. Furthermore, in certain implementations, less than or more than the operations described may be performed.

The word "exemplary" is used herein to mean "serving as an example, instance, or illustration." Any embodiment described herein as "exemplary" is not necessarily to be construed as preferred or advantageous over other embodiments. The terms "computing device," "user device," "communication station," "station," "handheld device." "mobile device," "wireless device" and "user equipment" (UE) as used herein refers to a wireless communication device such as a cellular telephone, a smartphone, a tablet, a netbook, a wireless terminal, a laptop computer, a femtocell, a high data rate (HDR) subscriber station, an access point, a printer, a point of sale device, an access terminal, or other personal communication system (PCS) device. The device may be either mobile or stationary.

As used within this document, the term "communicate" is intended to include transmitting, or receiving, or both transmitting and receiving. This may be particularly useful in claims when describing the organization of data that is being transmitted by one device and received by another, but only the functionality of one of those devices is required to infringe the claim. Similarly, the bidirectional exchange of data between two devices (both devices transmit and receive during the exchange) may be described as "communicating." when only the functionality of one of those devices is being claimed. The term "communicating" as used herein with respect to a wireless communication signal includes transmitting the wireless communication signal and/or receiving the wireless communication signal. For example, a wireless communication unit, which is capable of communicating a wireless communication signal, may include a wireless transmitter to transmit the wireless communication signal to at least one other wireless communication unit, and/or a wireless communication receiver to receive the wireless communication signal from at least one other wireless communication unit.

As used herein, unless otherwise specified, the use of the ordinal adjectives "first," "second." "third," etc., to describe a common object, merely indicates that different instances of like objects are being referred to and are not intended to imply that the objects so described must be in a given sequence, either temporally, spatially, in ranking, or in any other manner.

Some embodiments may be used in conjunction with various devices and systems, for example, a personal computer (PC), a desktop computer, a mobile computer, a laptop computer, a notebook computer, a tablet computer, a server computer, a handheld computer, a handheld device, a personal digital assistant (PDA) device, a handheld PDA device, an on-board device, an off-board device, a hybrid device, a vehicular device, a non-vehicular device, a mobile or portable device, a consumer device, a non-mobile or non-portable device, a wireless communication station, a wireless communication device, a wireless access point (AP), a wired or wireless router, a wired or wireless modem, a video device, an audio device, an audio-video (A/V) device, a wired or wireless network, a wireless area network, a wireless video area network (WVAN), a local area network (LAN), a wireless LAN (WLAN), a personal area network (PAN), a wireless PAN (WPAN), and the like.

Some embodiments may be used in conjunction with one way and/or two-way radio communication systems, cellular radio-telephone communication systems, a mobile phone, a cellular telephone, a wireless telephone, a personal communication system (PCS) device, a PDA device which incorporates a wireless communication device, a mobile or portable global positioning system (GPS) device, a device which incorporates a GPS receiver or transceiver or chip, a device which incorporates an RFID element or chip, a multiple input multiple output (MIMO) transceiver or device, a single input multiple output (SIMO) transceiver or device, a multiple input single output (MISO) transceiver or device, a device having one or more internal antennas and/or external antennas, digital video broadcast (DVB) devices or systems, multi-standard radio devices or systems, a wired or wireless handheld device, e.g., a smartphone, a wireless application protocol (WAP) device, or the like.

Some embodiments may be used in conjunction with one or more types of wireless communication signals and/or systems following one or more wireless communication protocols, for example, radio frequency (RF), infrared (IR), frequency-division multiplexing (FDM), orthogonal FDM (OFDM), time-division multiplexing (TDM), time-division multiple access (TDMA), extended TDMA (E-TDMA), general packet radio service (GPRS), extended GPRS, code-division multiple access (CDMA), wideband CDMA (WCDMA), CDMA 2000, single-carrier CDMA, multi-carrier CDMA, multi-carrier modulation (MDM), discrete multi-tone (DMT), Bluetooth®, global positioning system (GPS), Wi-Fi, Wi-Max, ZigBee, ultra-wideband (UWB), global system for mobile communications (GSM), 2G, 2.5G, 3G, 3.5G, 4G, fifth generation (5G) mobile networks, 3GPP, long term evolution (LTE), LTE advanced, enhanced data rates for GSM Evolution (EDGE), or the like. Other embodiments may be used in various other devices, systems, and/or networks.

It is understood that the above descriptions are for purposes of illustration and are not meant to be limiting.

Although specific embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Further, while various illustrative implementations and architectures have been described in accordance with embodiments of the disclosure, one of ordinary skill in the art will appreciate that numerous other modifications to the illustrative implementations and architectures described herein are also within the scope of this disclosure.

Program module(s), applications, or the like disclosed herein may include one or more software components including, for example, software objects, methods, data structures, or the like. Each such software component may include computer-executable instructions that, responsive to execution, cause at least a portion of the functionality described herein (e.g., one or more operations of the illustrative methods described herein) to be performed.

A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform.

Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, or a report writing language. In one or more example embodiments, a software component comprising instructions in one of the foregoing examples of programming languages may be executed directly by an operating system or other software component without having to be first transformed into another form.

A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

Software components may invoke or be invoked by other software components through any of a wide variety of mechanisms. Invoked or invoking software components may comprise other custom-developed application software, operating system functionality (e.g., device drivers, data storage (e.g., file management) routines, other common routines and services, etc.), or third-party software components (e.g., middleware, encryption, or other security software, database management software, file transfer or other network communication software, mathematical or statistical software, image processing software, and format translation software).

Software components associated with a particular solution or system may reside and be executed on a single platform or may be distributed across multiple platforms. The multiple platforms may be associated with more than one hardware vendor, underlying chip technology, or operating system. Furthermore, software components associated with a particular solution or system may be initially written in one or more programming languages, but may invoke software components written in another programming language.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or operations specified in any applicable flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or operations specified in any flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program module(s), or other data transmitted within a data signal, such as a carrier wave, or other transmission. However, as used herein, CRSM does not include CRCM.

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A method for analyzing sleep efficiency using non-invasive measurements, the method comprising:
    receiving, by at least one processor of a device, photoplethysmography (PPG) data;
    receiving, by the at least one processor, accelerometer data indicative of motion;
    determining, by the at least one processor, a first time period during which the accelerometer data is below a motion threshold;
    determining, by the at least one processor, a first periodic duration of the PPG data, the first periodic duration occurring during the first time period;
    determining, by the at least one processor, a second periodic duration of the PPG data, the second periodic duration occurring during the first time period;
    determining, by the at least one processor, that the first periodic duration is smaller than the second periodic duration;
    determining, by the at least one processor, based on the first periodic duration being smaller than the second periodic duration, that the first periodic duration is indicative of an inhalation period and that second periodic duration is indicative of an exhalation period;
    determining, by the at least one processor, a first portion of the first periodic duration of the PPG data that fails to exceed a threshold frequency;
    determining, by the at least one processor, a second portion of the first periodic duration of the PPG data that exceeds the threshold frequency;
    determining, by the at least one processor, a ratio of the first portion to the second portion;
    determining, by the at least one processor, a peak inspiratory flow during the first periodic duration and based on a number of times that the first periodic duration and the second periodic duration occur during a second time period;
    determining, by the at least one processor, based on the ratio, the peak inspiratory flow, and the first time period, a sleep efficiency score;
    determining, by the at least one processor, based on the accelerometer data, a recommended activity associated with increasing the sleep efficiency score; and
    causing presentation, by the at least one processor, of the sleep efficiency score and the recommended activity.

2. The method of claim 1, wherein the sleep efficiency score is associated with a first time, the method further comprising:
    determining a second sleep efficiency score associated with a second time preceding the first time; and
    determining that the recommended activity is associated with the second sleep efficiency score at the second time,
    wherein determining the recommended activity is further based on the determination that the recommended activity is associated with the second sleep efficiency score at the second time.

3. The method of claim 1, wherein the sleep efficiency score is a forecasted sleep efficiency score.

4. The method of claim 1, further comprising determining a scheduled activity based on calendar data, wherein determining the recommended activity is further based on the scheduled activity.

5. A method for analyzing sleep efficiency using non-invasive measurements, the method comprising:
    receiving, by at least one processor of a device, photoplethysmography (PPG) data;
    determining, by the at least one processor, a first periodic duration of the PPG data;
    determining, by the at least one processor, a second periodic duration of the PPG data, wherein the first periodic duration is smaller than the second periodic duration;
    determining, by the at least one processor, based on the first periodic duration being smaller than the second periodic duration, that the first periodic duration is indicative of an inhalation period and that second periodic duration is indicative of an exhalation period;
    determining, by the at least one processor, an inspiratory flow during the first periodic duration and based on a number of times that the first periodic duration and the second periodic duration occur during a first time period;

determining, by the at least one processor, based on the inhalation period, a sleep efficiency score; and causing presentation, by the at least one processor, of the sleep efficiency score.

6. The method of claim 5, wherein the sleep efficiency score is a forecasted sleep efficiency score.

7. The method of claim 5, further comprising:
determining, by the at least one processor, a first portion of the PPG data that fails to exceed a threshold frequency;
determining, by the at least one processor, a second portion of the PPG data that exceeds the threshold frequency;
determining, by the at least one processor, a ratio of the first portion to the second portion; and
determining, by the at least one processor, based on the first periodic duration of the PPG data, a metric comprising the ratio,
wherein determining the sleep efficiency score is further based on the metric.

8. The method of claim 5, wherein the inspiratory flow is a peak inspiratory flow.

9. The method of claim 5, further comprising determining a recommended activity associated with increasing the sleep efficiency score, wherein the recommended activity comprises at least one of bed time, a wake time, or exercise.

10. The method of claim 5, further comprising:
determining that performance of an activity will improve the sleep efficiency score; and
causing presentation of an indication that performance of the activity will improve the sleep efficiency score.

11. The method of claim 5, further comprising:
receiving data indicative of device motion; and
determining that the device motion is associated with an activity,
wherein determining the sleep efficiency score is further based on the activity.

12. The method of claim 5, further comprising:
receiving accelerometer data indicative of device motion; and
determining a second time period during which the accelerometer data is below a motion threshold,
wherein the first periodic duration and the second periodic duration of the PPG data occur during the second time period.

13. The method of claim 5, further comprising:
determining a scheduled activity based on calendar data;
determining a recommended activity based on the scheduled activity, the recommended activity associated with increasing the sleep efficiency score; and
causing presentation of the recommended activity.

14. The method of claim 5, wherein the sleep efficiency score is associated with a first time, the method further comprising:
determining a sleep efficiency score associated with a second time preceding the first time; and
determining second PPG data associated with the sleep efficiency score,
wherein determining the sleep efficiency score is further based on the second PPG data.

15. The method of claim 5, further comprising:
receiving accelerometer data indicative of device motion;
determining a second time period during which the accelerometer data is below a motion threshold;
determining a third time period during which the accelerometer data is below the motion threshold;
determining a third periodic duration of the PPG data that occurs during the second third time period; and
determining, that the third periodic duration of the PPG data is indicative of a second inhalation period,
wherein determining the sleep efficiency score is further based on the second inhalation period.

16. The method of claim 5, further comprising determining, based on the sleep efficiency score, using a machine learning model, one or more sleep stages.

17. A wearable device for analyzing sleep efficiency using non-invasive measurements, the wearable device comprising:
a photodiode; and
memory coupled to at least one processor, the at least one processor configured to:
emit a light wave using the photodiode;
receive a reflection of the light wave using the photodiode;
determine, based on the reflection, photoplethysmography (PPG) data;
determine a first periodic duration of the PPG data;
determine a second periodic duration of the PPG data, wherein the first periodic duration is smaller than the second periodic duration;
determine, based on the first periodic duration being smaller than the second periodic duration, that the first periodic duration is indicative of an inhalation period and that second periodic duration is indicative of an exhalation period;
determine an inspiratory flow during the first periodic duration and based on a number of times that the first periodic duration and the second periodic duration occur during a first time period;
determine, based on the inhalation period, a sleep efficiency score; and
cause presentation of the sleep efficiency score.

18. The wearable device of claim 17, wherein the at least one processor is further configured to:
determine that performance of an activity will improve the sleep efficiency score; and
cause presentation of an indication that performance of the activity will improve the sleep efficiency score.

19. The wearable device of claim 17, wherein the at least one processor is further configured to:
receive data indicative of device motion; and
determine that the device motion is associated with an activity,
wherein to determine the sleep efficiency score is further based on the activity.

20. The wearable device of claim 17, wherein the at least one processor is further configured to:
receive accelerometer data indicative of device motion; and
determine a second time period during which the accelerometer data is below a motion threshold and is greater than zero,
wherein the first periodic duration and the second periodic duration of the PPG data occur during the second time period.

* * * * *

UNITED STATES PATENT AND TRADEMARK OFFICE
CERTIFICATE OF CORRECTION

PATENT NO. : 12,121,362 B1
APPLICATION NO. : 17/018796
DATED : October 22, 2024
INVENTOR(S) : Pekka Pietari Pulkkinen, Andreas Caduff and Haithem Albadawi It is certified that error appears in the above-identified patent and that said Letters Patent is hereby corrected as shown below:

In the Claims

Claim 15 at Column 26, Line 6, should read -- occurs during the third time period; and --.

Signed and Sealed this
Third Day of December, 2024

Katherine Kelly Vidal
*Director of the United States Patent and Trademark Office*